US010206399B2

(12) United States Patent
Kim et al.

(10) Patent No.: US 10,206,399 B2
(45) Date of Patent: Feb. 19, 2019

(54) HERBICIDAL COMPOSITION COMPRISING URACIL COMPOUND AS ACTIVE INGREDIENT

(71) Applicant: Dongbu Farm Hannong Co., Ltd., Seoul (KR)

(72) Inventors: Kyoung Sung Kim, Seoul (KR); In Young Choi, Daejeon (KR); Mi Sook Hong, Seoul (KR); Tae Joon Kim, Daejeon (KR); Jun Hyuk Choi, Daejeon (KR); Gi Jun Moon, Daejeon (KR); Kyoung Sung Kim, Daejeon (KR)

(73) Assignee: Dongbu Farm Hannong Co., Ltd., Seoul (KR)

( * ) Notice: Subject to any disclaimer, the term of this patent is extended or adjusted under 35 U.S.C. 154(b) by 0 days.

(21) Appl. No.: 14/508,692

(22) Filed: Oct. 7, 2014

(65) Prior Publication Data

US 2015/0024940 A1   Jan. 22, 2015

Related U.S. Application Data

(63) Continuation of application No. PCT/KR2013/003107, filed on Apr. 12, 2013.

(30) Foreign Application Priority Data

Apr. 12, 2012 (KR) ........................ 10-2012-0038002

(51) Int. Cl.

| *A01N 35/10* | (2006.01) |
| *A01N 37/22* | (2006.01) |
| *A01N 37/40* | (2006.01) |
| *A01N 39/02* | (2006.01) |
| *A01N 39/04* | (2006.01) |
| *A01N 41/10* | (2006.01) |
| *A01N 43/40* | (2006.01) |
| *A01N 43/42* | (2006.01) |
| *A01N 43/50* | (2006.01) |
| *A01N 43/54* | (2006.01) |
| *A01N 43/76* | (2006.01) |
| *A01N 43/80* | (2006.01) |
| *A01N 43/82* | (2006.01) |
| *A01N 43/88* | (2006.01) |
| *A01N 43/90* | (2006.01) |
| *A01N 47/36* | (2006.01) |
| *A01N 57/20* | (2006.01) |
| *A01N 43/653* | (2006.01) |

(52) U.S. Cl.
CPC ............ *A01N 43/54* (2013.01); *A01N 41/10* (2013.01); *A01N 43/40* (2013.01); *A01N 43/653* (2013.01); *A01N 43/80* (2013.01); *A01N 43/82* (2013.01); *A01N 43/90* (2013.01); *A01N 47/36* (2013.01); *A01N 57/20* (2013.01)

(58) Field of Classification Search
CPC ...................................................... A01N 59/20
See application file for complete search history.

(56) References Cited

U.S. PATENT DOCUMENTS

| 6,159,899 | A  | * | 12/2000 | Hudetz ................. A01N 43/54 504/130 |
| 6,617,281 | B1 |   | 9/2003  | Andree et al. |
| 6,734,139 | B1 |   | 5/2004  | Feucht et al. |
| 2004/0171488 | A1 |   | 9/2004  | Feucht et al. |
| 2006/0025591 | A1 |   | 2/2006  | Meazza et al. |
| 2011/0224083 | A1 | * | 9/2011  | Ko ........................ A01N 43/54 504/243 |

FOREIGN PATENT DOCUMENTS

| CN | 102203071 A | 9/2011 |
| EP | 0714602 A1 | 6/1996 |
| EP | 1605758 B1 | 12/2005 |
| EP | 2343284 A2 | 7/2011 |
| JP | 11-189506 A | 7/1999 |
| JP | 2012504599 A | 2/2012 |
| KR | 10-2010-0038052 A | 4/2010 |
| WO | 96/07323 A1 | 3/1996 |
| WO | WO-2004/080183 A1 | 9/2004 |
| WO | WO-2007/014758 A1 | 2/2007 |
| WO | WO 2010/038953 | * | 4/2010 |
| WO | 2011-057935 A1 | 5/2011 |

OTHER PUBLICATIONS

Rummens, F.H.A., "An improved definition of synergistic and antagonistic effects," Weed Science, vol. 23 (1), pp. 4-6 (1975).*
Colby, S.R., "Calculating synergistic and antagonistic responses of herbicide combinations," Weeds, vol. 15 (1), pp. 20-22 (1967).*
Richer, D.L., "Synergism—a patent view," Pesticide Science, vol. 19, pp. 309-315 (1987).*
Chinese Office Action for Chinese Application No. 2013800192607, dated Jul. 21, 2015, 16 pages.
Colombian Office Action for Colombian Application No. 14-225781 dated Dec. 1, 2015, 10 pages.

* cited by examiner

*Primary Examiner* — John Pak
(74) *Attorney, Agent, or Firm* — Mintz Levin Cohn Ferris Glovsky and Popeo, P.C.; Kongsik Kim; Moonkyoung Um

(57) ABSTRACT

The present invention relates to a herbicidal composition comprising, as active ingredients, a herbicidally active compound and an uracil compound or an agrochemically acceptable salt thereof. The herbicidal composition has excellent effects not only on selective control of monocotyledonous or dicotyledonous weeds in useful crop plants, but also on control of monocotyledonous or dicotyledonous weeds in semi-selective or non-selective areas.

5 Claims, No Drawings

HERBICIDAL COMPOSITION COMPRISING URACIL COMPOUND AS ACTIVE INGREDIENT

CROSS-REFERENCE TO RELATED APPLICATIONS

This is a continuation of International Application No. PCT/KR2013/003107 filed on Apr. 12, 2013, which claims priority to Korean Application No. 10-2012-0038002 filed on Apr. 12, 2012. The applications are incorporated herein by reference.

TECHNICAL FIELD

The present invention relates to a herbicidal composition comprising a uracil compound as an active ingredient.

RELATED ART

Uracil compounds are known as useful herbicidally active compounds. German Patent Publication No. 714,602, International Patent Publication No. WO 96/07323 and Japanese Patent Laid-Open Publication No. Hei 11-189506 disclose herbicidal compositions comprising a uracil compound as an active ingredient. Meanwhile, Korean Patent No. 1,103,840 registered in the name of the applicant discloses a novel uracil compound and a herbicidal composition comprising the same as an active ingredient.

However, there has been a continued demand for a broad-spectrum herbicidal composition which exhibits a remarkable synergistic effect higher than that of two or more herbicidally active compounds and has selective, semi-selective and/or non-selective activity against monocotyledonous and/or dicotyledonous weeds in various plants.

SUMMARY

Accordingly, an object of the present invention is to provide a herbicidal composition having a remarkable synergistic effect, which comprises a herbicidally active compound selected from uracil compounds and another herbicidally active compound.

Another object of the present invention is to provide a broad-spectrum herbicidal composition having selective, semi-selective and/or non-selective activity against monocotyledonous and/or dicotyledonous weeds in various plants, in which the herbicidal composition comprises a herbicidally active compound selected from uracil compounds and another herbicidally active compound.

The present invention provides a herbicidal composition comprising, as active ingredients, a herbicidally active compound and a uracil compound represented by the following formula 1 or an agrochemically acceptable salt thereof:

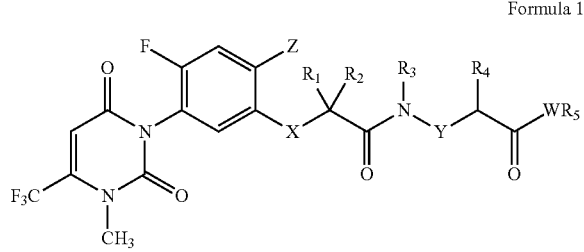

Formula 1 wherein
$R_1$ and $R_2$ are the same or different and represent a hydrogen atom or a $C_1$-$C_6$ alkyl group; $R_3$ represents a hydrogen atom, a hydroxyl group, a $C_1$-$C_6$ alkyl group, a $C_2$-$C_6$ alkenyl group, a $C_2$-$C_6$ alkynyl group, a $C_1$-$C_8$ alkoxy group, a $C_1$-$C_6$ haloalkyl group, a $C_2$-$C_6$ haloalkenyl group, a $C_1$-$C_6$ alkoxy $C_1$-$C_6$ alkyl group, or a $C_6$-$C_{10}$ aryl $C_1$-$C_6$ alkoxy group; $R_4$ represents a hydrogen atom, a $C_1$-$C_6$ alkyl group, a $C_1$-$C_6$ haloalkyl group, or a $C_1$-$C_6$ alkoxycarbonyl $C_1$-$C_6$ alkyl group; $R_5$ represents a hydrogen atom, a $C_1$-$C_6$ alkyl group, a $C_1$-$C_6$ alkoxy group, a $C_2$-$C_6$ haloalkyl group, a $C_2$-$C_6$ alkenyl group, a $C_2$-$C_6$ haloalkenyl group, a $C_2$-$C_6$ alkynyl group, a $C_1$-$C_6$ alkoxycarbonyl group, a $C_1$-$C_6$ alkyl group, a $C_6$-$C_{10}$ aryl $C_1$-$C_6$ alkyl group, or a $C_6$-$C_{10}$ aryl $C_1$-$C_6$ alkoxy group; X represents O, S, SO, $SO_2$, NH, or N($C_1$-$C_6$ alkyl); Y represents a $C_1$-$C_6$ alkylene group or a $C_1$-$C_6$ haloalkylene group; W represents O, S, NH, or N($C_1$-$C_6$ alkyl); and Z represents a halogen atom, a cyano group, $CONH_2$, or $CSNH_2$.

DETAILED DESCRIPTION

To achieve the above objects, the present invention provides a herbicidal composition comprising, as active ingredients, a herbicidally active compound and a uracil compound represented by the following formula 1 or an agrochemically acceptable salt thereof:

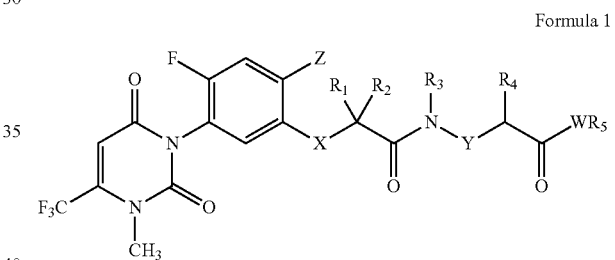

Formula 1

In Formula 1,
$R_1$ and $R_2$ are the same or different and represent a hydrogen atom or a $C_1$-$C_6$ alkyl group; $R_3$ represents a hydrogen atom, a hydroxyl group, a $C_1$-$C_6$ alkyl group, a $C_2$-$C_6$ alkenyl group, a $C_2$-$C_6$ alkynyl group, a $C_1$-$C_8$ alkoxy group, a $C_1$-$C_6$ haloalkyl group, a $C_2$-$C_6$ haloalkenyl group, a $C_1$-$C_6$ alkoxy $C_1$-$C_6$ alkyl group, or a $C_6$-$C_{10}$ aryl $C_1$-$C_6$ alkoxy group; $R_4$ represents a hydrogen atom, a $C_1$-$C_6$ alkyl group, a $C_1$-$C_6$ haloalkyl group, or a $C_1$-$C_6$ alkoxycarbonyl $C_1$-$C_6$ alkyl group; $R_5$ represents a hydrogen atom, a $C_1$-$C_6$ alkyl group, a $C_1$-$C_6$ alkoxy group, a $C_2$-$C_6$ haloalkyl group, a $C_2$-$C_6$ alkenyl group, a $C_2$-$C_6$ haloalkenyl group, a $C_2$-$C_6$ alkynyl group, a $C_1$-$C_6$ alkoxycarbonyl group, a $C_1$-$C_6$ alkyl group, a $C_6$-$C_{10}$ aryl $C_1$-$C_6$ alkyl group, or a $C_6$-$C_{10}$ aryl $C_1$-$C_6$ alkoxy group; X represents O, S, SO, $SO_2$, NH, or N($C_1$-$C_6$ alkyl); Y represents a $C_1$-$C_6$ alkylene group or a $C_1$-$C_6$ haloalkylene group; W represents O, S, NH, or N($C_1$-$C_6$ alkyl); and Z represents a halogen atom, a cyano group, $CONH_2$, or $CSNH_2$.

In one embodiment of the present invention, the uracil compound is 3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid methyl ester, or 3-[{2-[2-chloro-5-(3,6-dihydro-3-methyl-2,6-dioxo-4-trifluoromethyl-1(2H)-pyrimidinyl)-4-fluorophenylthio]-1-oxopropyl}amino]propionic acid methyl ester.

In one embodiment of the present invention, the herbicidally active compound is one or more selected from among amide derivatives, arylheterocycle derivatives, aryloxyphenoxy propionate derivatives, carboxylic acid derivatives, benzothiadiazole derivatives, chloroacetamide derivatives, cyclohexanedione derivatives, diphenyl ether derivatives, urea derivatives, imidazolidinone derivatives, isoxazole derivatives, nicotine anilide derivatives, nitrile derivatives, organic phosphorus compounds, oxyacetamide derivatives, phenoxycathoxylic acid derivatives, pyrazole derivatives, pyridazinone derivatives, pyridine derivatives, pyrimidinyl(thio)benzoate derivatives, sulfonylurea derivatives, tetrazolinone derivatives, thiocarbamate derivatives, triazine derivatives, triazinone derivatives, triazolinone derivatives, triazolopyrimidine derivatives, triketone derivatives, and uracil derivatives. In one embodiment of the present invention, the herbicidally active compound is one or more selected from among 2-chloro-N-(ethoxymethyl)-N-(2-ethyl-6-methyl-phenyl)-acetamide (acetochlor), 5-(2-chloro-4-trifluoromethyl-phenoxy)-2-nitro-benzoic acid sodium salt (acifluorfen-sodium), 2-chloro-6-nitro-3-phenoxy-benzenamine (aclonifen), 2-chloro-N-(methoxymethyl)-N-(2,6-diethyl-phenyl)-acetamide (alachlor), N-ethyl-N'-isopropyl-6-methylthio-1,3,5-triazine-2,4-diamine (ametryn), 4-amino-N-(1,1-dimethyl-ethyl)-4,5-dihydro-3-(1-methyl-ethyl)-5-oxo-1H-1,2,4-triazole-1-carboxamide (amicarbazone), N-(4,6-dimethoxy-pyrimidin-2-yl)-N'-(N-methyl-N-methylsulphonyl-sulphamoyl)-urea (amidosulfuron), 1H-1,2,4-triazol-3-amine (amitrole), 6-chloro-4-ethylamino-2-isopropylamino-1,3,5-triazine (atrazine), 2-[2,4-dichloro-5-(2-propinyloxy)-phenyl]-5,6,7,8-tetrahydro-1,2,4-triazolo-[4,3-a]-pyridin-3(2H)-one (azafenidin), N-(4,6-dimethoxy-pyrimidin-2-yl)-N'-1-[methyl-4-(2-methyl-2H-tetrazol-5-yl)-1H-pyrazol-5-ylsulphonyl]-urea (azimsulfuron), N-benzyl-2-(4-fluoro-3-trifluoromethyl-phenoxy)-butanamide (beflubutamid), 4-chloro-2-oxo-3(2H)-benzothiazoleacetic acid (benazolin), N-butyl-N-ethyl-2,6-dinitro-4-trifluoromethyl-benzenamine (benfluralin), N-(4,6-dimethoxy-pyrimidin-2-yl)-N-(2-methoxycarbonyl-phenylmethylsulphonly)-urea (bensulfuron), methyl 2-[2-[4-(3,6-dihydro-3-methyl-2,6-dioxo-4-trifluoromethyl-1 (2H)-pyrimidinyl)phenoxy]methyl]-5-ethyl-phenoxy-propanoate (benzfendizone), 3-(2-chloro-4-methylsulphonyl-benzoyl)-4-phenylthio-bicyclo-[3.2.1]-oct-3-en-2-one (benzobicyclon), ethyl N-benzoyl-N-(3,4-dichloro-phenyl)-DL-alaninate (benzoylprop-ethyl), 3-i-propyl-1H-2,1,3-benzothiadiazin-4(3H)-one (bentazone), methyl 5-(2,4-dichloro-phenoxy)-2-nitro-benzoate (bifenox), 2,6-bis-4,6-dimethyoxy-pyrimidin-2-yl-oxy)-benzoic acid sodium salt (bispyribac-sodium), 5-bromo-6-methyl-3-(1-methyl-propyl)-2,4(1H,3H)pyrimidinedione (bromacil), 2-bromo-3,3-dimethyl-N-(1-methyl-1-phenyl-ethyl)-butanamide (bromobutide), O-(2,4-dinitro-phenyl) 3,5-dibromo-4-hydroxy-benzaldehyde-oxime (bromofenoxim), 3,5-dibromo-4-hydroxy-benzonitrile (bromoxynil), N-butoxymethyl-2-chloro-N-(2,6-diethyl-phenyl)-acetamide (butachlor), [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), S-ethyl bis-(2-methyl-propyl)-thiocarbamate (butylate), N,N-diethyl-3-(2,4,6-trimethyl-phenylsulphonyl)-1H-1,2,4-triazole-1-carboxamide (cafenstrole), 2-1-[(3-chloro-2-propenyl)-oxy-imino-propyl]-3-hydroxy-5-(tetrahydro-2H-pyran-4-yl)-2-cyclo-hexen-1-one (caloxydim, tepraloxydim), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl), 2,4-dichloro-1-(3-methoxy-4-nitro-phenoxy)-benzene (chlomethoxyfen), 3-amimo-2,5-dichloro-benzoic acid (chloramben), N-(4-chloro-6-methoxy-pyrimdin-2-yl)-N-(2-ethoxycarbonyl-phenylsulphonyl)-urea (chlorimuron-ethyl), 1,3,5-trichloro-2-(4-nitro-phenoxy)-benzene (clomitrofen), N-(4-methoxy-6-methyl-1,3,5-triazin-2-yl)-N-(2-chloro-phenylsulphonyl)-urea (chlorsulfuron), N-(3-chloro-4-methylphenyl)-N,N-dimethyl-urea (chlortoluron), ethyl 2-chloro-3-[2-chloro-5-(1,3,4,5,6,7-hexahydro-1,3-dioxo-2H-isoindol-2-yl)-phenyl]-2-propanoate (cinidon-ethyl), N-(4,6-dimethoxy-1,3,5-triazin-2-yl)-N'-(2-(2-methoxy-ethoxy)-phenylsulphonyl)-urea (cinosulfuron), 2-[1-[2-4-chloro-phenoxy)-propoxyamino]butyl]-5-(tetrahydro-2H-thiopyran-3-yl)-1,3-cyclohexanedione (clefoxydim), (E,E)-(+)-2-[1-[[(3-chloro-2-propenyl)-oxy]-imino]-propyl]-3-hydroxy-2-cyclohexen-1-one (clethodim), prop-2-inyl (R)-2-[4-(5-chloro-3-fluoro-pyridin-2-yl-oxy)-phexoxyl]-propanoate (clodinafop-propargyl), 3,6-dichloro-pyridine-2-carboxylic acid (clopyralid), methyl 3-chloro-2-[(5-ethoxy-7-fluoro[1,2,4]triazolo[1,5-c]pyrimidin-2-yl-sulphonyl)-amino]-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), 2,4-dichloro-phenoxyacetic acid (2,4-D), 3,6-dichloro-2-methoxy-benzoic acid (dicamba), (R)-2-(2,4-dichloro-phenoxy)-propanoic acid (dichlorprop-P), methyl-2-[4-(2,4-dichloro-phenoxy)-phenoxy]-propanoate (diclofop-methyl), N-(2,6-dichloro-phenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methylsulphate (difenzoquat), N-(2,4-difluoro-phenyl)-2-(3-trifluoromethyl-phenoxy)-pyridine-3-carboxamide (diflufenican), 2-[1-(3,5-difluoro-phenyl)-amino-carbonyl-hydrazono-ethyl]-pyridine-3-carboxylic acid (diflufenzopyr), S-(1-methyl-1-phenyl-ethyl) 1-piperidine-carbothioate (dimepiperate), 2-chloro-N-(2,6-dimethyl-phenyl)-N-(2-methoxy-ethyl)-acetamide (dimethachlor), (S)2-chloro-N-(2,4-dimethyl-3-thienyl)-N-(2-methoxy-1-methyl-ethyl)-acetamide (S) (dimethenamid), 2-amino-4-(1-fluoro-1-methyl-ethyl)-6-(1-methyl-2-(3,5-dimethyl-phenoxy)-ethylamino)-1,3,5-triazine (dimexyflam), N3,N3-diethyl-2,4-dinitro-6-trifluoromethyl-1,3-diamino-benzene (dinitramine), 6,7-dihydro-dipyrido[1,2-a:2,1-c]pyrazinediium (diquat), S,S-dimethyl 2-difluoromethyl-4-i-butyl-6-trifluoromethyl-pyridine-3,5-dicarbothioate (dithiopyr), N'-(3,4-dichloro-phenyl)-N,N-dimethyl-urea (diuron), 2-2-(3-chloro-phenyl)-oxiranylmethyl-2-ethyl-1H-indene-1,3(2H)-dione (epropodan), S-ethyl di-propylthiocarbamate (EPTC), S-(phenylmethyl) N-ethyl-N-(1,2-dimethylpropyl)-thiocarbamate (esprocarb), N-ethyl-N-(2-methyl-2-propenyl)-2,6-dinitro-4-trifluoromethyl-benzenamine (ethalfluralin), 2-ethoxy-1-methyl-2-oxoethyl (S)-2-chloro-5-(2-chloro-4-trifluoromethyl-phenoxy)-benzoate (ethoxyfen), N-(4,6-dimethoxy-pyrimidin-2-yl)-N'-(2-ethoxy-phenoxysulphonyl)-urea (ethoxysulfuron), ethyl (R)-2-[4-(6-chloro-benzoxazol-2-yl-oxy)-phenoxy]-propanoate (fenoxaprop-(P)-ethyl), 4-(2-cholor-phenyl)-N-cyclohexyl-N-ethyl-4,5-dihydro-5-oxo-1H-tetrazole-1-carboxamide (fentrazamid), isopropyl N-benzoyl-N-(3-chloro-4-fluoro-phenyl)-DL-alaninate (flamprop-isopropyl), isopropyl N-benzoyl-N-(3-chloro-4- fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, P-butyl), i-propyl 5-(4-bromo-1-methyl-5-trifluoromethyl-1H-pyrazol-3-yl)-2-chloro-4-fluoro-benzoate (fluazolate), 4,5-(dihydro)-3-methoxy-4-methyl-5-oxo-N-[(2-trifluoromethoxy-phenyl)-sulphonyl]-1H-1,2,4-triazole-1-carboxamide sodium salt (flucarbazone-sodium), N-(4-fluoro-phenyl)-N-i-propyl-2-(5-trifluoromethyl-1,3,4-thiadiazol-2-yl-oxy)-acetamide (flufenacet), N-(2,6-difluoro-phenyl)-5-methyiyl-1,2,4-triazolo[1,5-a]-pyrimidine-2-sulphonamide (flumetsulam), pentyl [2-chloro-4-fluoro-5-(1,3,4,5,6,7-hexahydro-1,3-dioxo-2H-isoindol-2-yl)-phenoxy]-acetate (flumiclorac-pentyl), 2-[7-fluoro-3,4-dihydro-3-oxo-4-(2-propinyl)-2H-1,4-benzoxazin-6-yl]-4,5,6,7-tetrahydro-1H-isoindole-1,3-dione (flumioxazin), 2-[4-chloro-2-fluoro-5-(1-methyl-2-propinyl)-oxy]-phenyl-4,5,6,7-tetrahydro-1H-isoindole-1,3(2H)-dione (flumipropyn), 3-chloro-4-chloromethyl-1-(3-trifluoromethyl-phenyl)-2-pyrrolidinone (fluorochloridone), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1(2H)-pyrimidyl)-benzoate (flupropacil), N-(4,6-dimethoxy-pyrimidin-2-yl)-N'-(3-methoxycarbonyl-6-trifluoromethyl-pyridin-2-yl-sulphonyl)-urea sodium salt (flupyrsulfuron-methyl-sodium), 9-hydroxy-9H-fluorene-9-carboxylic acid (flurenol), (4-amino-3,5-dichloro-6-fluoro-pyridin-2-yl-oxy)-acetic acid (2-butoxy-1-methyl-ethyl ester, 1-methyl-heptyl ester) (fluroxypyr, -butoxypropyl, -meptyl), 5-methylamino-2-phenyl-4-(3-trifluoromethyl-phenyl)-3(2H)-furanone (flurtamone), methyl [(2-chloro-4-fluoro-5-(tetrahydro-3-oxo-1H,3H-[1,3,4]-thiadiazolo-[3,4-a]-pyridazin-1-yliden)-amino)-phenyl-thioacetate (fluthiacet-methyl), 5-(2-chloro-4-trifluoromethyl-phenoxy)-N-methylsulphonyl-2-nitro-benzamide (fomesafen), 2-[[[[(4,6-dimethoxy-2-pyrimidinyl)-amino]-carbonyl]-amino]-sulphonyl]-4-formylamino-N,N-dimethyl-benzamide (foramsulfuron), 2-amino-4-(hydroxymethylphosphinyl)-butanoic acid ammonium salt (glufosinate-ammonium), N-phosphonomethyl-glycine (isopropylammonium salt) (glyphosate, isopropylammonium), (R)-2-[4-(3-chloro-5-trifluoromethyl-pyridin-2-yl-oxy)-phenoxy]-propanoci acid (methyl ester, 2-ethoxy-ethyl ester, butyl ester) (haloxyfop, -methyl, P-methyl, -ethoxyethyl, -butyl), 3-cyclohexyl-6-dimethyl-amino-1-methyl-1,3,5-triazine-2,4(1H,3H)-dione (hexazinone), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazoi-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo-[1,2-a]-pyridin-3-yl-sulphonyl)urea (imazosulfuron), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (4-chloro-2-methylsulphonyl-phenyl)-(5-cyclopropyl-isoxazol-4-yl)-methanone (isoxachlortole), (5-cyclopropyl-isoxazol-4-yl)-(2-methylsulphonyl-4-trifluoromethyl-phenyl)-methanone (isoxaflutole), 2-[2-[4-[(3,5-dichloro-2-pyridinyl)-oxy]-phenyl]-1-oxo-propyl]-isoxazolidine (isoxapyrifop), (2-ethoxy-1-methyl-2-oxo-ethyl)-5-(2-chloro-4-trifluoromethyl-phenoxy)-2-nitro-benzoate (lactofen), N-(3,4-dichloro-phenyl)-N-methoxy-N-methyl-urea (linuron), (4-chloro-2-methyl-phenoxy)-acetic acid (MCPA), (±)-2-(4-chloro-2-methyl-phenoxy)-proponic acid (mecoprop), 2-(2-benzothiazolyloxy)-N-methyl-N-phenyl-acetamide (mefenacet), methyl [[[[2-(4,6-dimethoxy-2-pyrimidinyl)amino]carbonyl]amino]sulphonyl]-4-[[(methylsulphonyl)amino]methyl]-benzoate (mesosulfuron), 2-(4-methylsulphonyl-2-nitro-benzoyl)-1,3-cyclohexanedione (mesotrione), 4-amino-3-methyl-6-phenyl-1,2,4-triazin-5(4H)-one (metamitron), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H-1-benzopyran-7-yl-oxy)-phenyl)-N-methoxy-N-methyl-urea (metobenzuron), N'-(4-bromophenyl)-N-methoxy-N-methyl urea (metobromuron), (S)-2-chloro-N-(2-ethyl-6-methyl-phenyl)-N-(2-methoxy-1-methyl-ethyl)acetamide (metolachlor, S-metolachlor), N-(2,6-dichloro-3-methyl-phenyl)-5,7-dimethoxy-1,2,4-triazolo[1,5-a]-pyrimidine-2-sulphonamide (metosulam), N'-(3-chloro-4-methoxy-phenyl)-N,N-di-ethyl-urea (metoxuron), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), S-ethyl-hexahydro-1H-azepine-1-carbothioate (molinate), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), 4-chloro-5-methylamino-2-(3-trifluoromethyl-phenyl)-3(2H)-pyridazinone (norflurazon), S-(2-chloro-benzyl)-N,N-diethyl-thiocarbamate (orbencarb), 4-dipropylamino-3,5-dinitro-benzenesulphonamide (oryzalin), 3-[2,4-dichloro-5-(2-propinyloxy)-phenyl-5]-(t-butyl)-1,3,4-oxadiazol-2(3H)-one (oxadiargyl), 3-2,4-dichloro-5-(1-methyl-ethoxy)-phenyl-5-(t-butyl)-1,3,4-oxadiazol-2(3H)-one (oxadiazon), N-(4,6-dimethyl-pyrimidin-2-yl)-N'-(2-oxetan-3-yl-oxycarbonyl-phenylsulphonyl)-urea (oxasulfuron), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethylbenzene (oxyfluorfen), 1,1'-dimethyl-4,4'-bipyridinium (paraquat), 1-amino-N-(1-ethyl-propyl)-3,4-dimethyl-2,6-dinitro-benzene (pendimethalin), 4-(t-butyl)-N-(1-ethyl-propyl)-2,6-dinitro-benzenamine (pendralin), 4-amino-3,5,6-trichloro-pyridime-2-carboxylic acid (picloram), N-(4-fluoro-phenyl)-6-(3-trifluoromethyl-phenoxy)-pyridine-2-carboxamide (picolinafen), 2-chloro-N-(2,6-diethyl-phenyl)-N-(2-propoxy-ethyl)-acetamide (pretilachlor), N-(4,6-bis-difluoromethoxy-pyrimidin-2-yl)-N'-(2-methoxycarbonyl-phenylsulphonyl)-urea (primisulfuron-methyl), 1-chloro-N-2-chloro-4-fluoro-5-[(6S,7aR)-6-fluorotetrahydro-1,3-dioxo-1H-pyrrolo[1,2-c]imidazol-2(3H)-yl-phenyl-methanesulphonamide (profluazol), 2-chloro-N-isopropyl-N-phenyl-acetamide (propachlor), N-(3,4-dichlorophenyl)-propanamide (propanil), (R)-[2-[[(1-methylethylidene)-amino]-oxy]-ethyl]-2-[4-(6-chloro-2-quinoxalinyloxy)-phenoxy]-propanoate (propaquiza-fop), 2-chloro-N-(2-ethyl-6-methyl-phenyl)-N-[(1-methylethoxy)-methyl]-acetamide (propisochlor), methyl [[[2-(4,5-dihydro-4-methyl-5-oxo-3-propoxy-1H-1,2,4-triazol-1-yl)-carbonyl]-amino]-sulphonyl]-benzoate sodium salt (propoxycarbazone-sodium), S-phenylmethyl N,N-dipropyl-thiocarbamate (prosulfocarb), N-(4-methoxy-6-methyl-1,3,5-triazin-2-yl)-N'-(2-(3,3,3-trifluror-propyl)-phenylsulphonyl)-urea (prosulfuron), elhyl [2-chloro-5-(4-chloro-5-difluoromethoxy-1-methyl-1H-pyrazol-3-yl)-4-fluorophenoxy]-acetate (pyraflufen-ethyl), 1-(3-chloro-4,5,6,7-tetrahydro-pyrazolo[1,5-a]pyridin-2-yl)-5-(methyl-2-propinylamino)-1H-pyrazole-4-carbonitrile (pyrazogyl), 4-(2,4-dichloro-benzoyl)-1,3-dimethyl-5-(4-methyl-phenylsulphonyloxy)-pyrazole (pyrazolate), 4-(2,4-dichloro-benzoyl)-1,3-dimethyl-5-(phenylcarbonylmethoxy)-pyrazole (pyrazoxyfen), N'-(4,6-dimethoxy-pyrimidin-2-yl)-N-(4-ethoxycarbonyl-1 methyl-pyrazol-5-yl-sulphonyl)-urea (pyrazosulfuron-ethyl), O-[2,6-bis-(4,6-dimethoxy-pyrimidin-2-yl-oxy)-benxoyl]diphenylmethanone-oxime (pyribenzoxim), 6-chloro-3-phenyl-4-pyridazinol (pyridafol), O-(6-chloro-3-phenyl-pyridazin-4-yl) S-octyl thiocarbonate (pyridate), 6-chloro-3-phenyl-pyridazin-4-ol (pyridatol), 7-[(4,6-dimethoxy-2-pyrimidinyl)-thio]-3-methyl-1(3H)-iso-benzofuranone (Pyriftalid), methyl 2-(4,6-dimethoxy-pyrimidin-2-yl-oxy)-benzoate (pyriminobac-methyl), 2-chloro-6-(4,6-dimethoxy-pyrimidin-2-ylthio)-benzoic acid sodium salt (pyrithiobac-sodium), 3,7-dichloro-quinoline-8-carboxylic acid (quinchlorac), 7-chloro-3-methyl-quinoline-8-carboxylic acid (quinmerac), 2-[4-(6-chloro-2-quinoxalinyloxy)-phenoxy]-propanic acid (ethyl-ester, tetrahydro-2-furanyl-methyl ester) (quizalofop, -ethyl, P-ethyl, P-tefuryl), N-(4,6-dimethoxy-pyrimidin-2-yl)-N'-(3-ethylsulphonyl-pyridin-2-yl-sulphonyl)-urea (rimsulfuron), 2-(1-ethoximinobutyl)-5-(2-ethylthiopropyl)-3-hydroxy-2-cyclohexen-1-one (sethoxydim), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone), methyl [[[2-(4,6-dimethyl-2-pyrimidinyl)amino]carbonyl]amino]sulphonyl]-benzoate (sulfometuron-methyl), N-phosphonomethyl-glycine-trimethylsulphonium (sulfonate), N-(4,6-dimethoxy-pyrimidin-2-yl)-N'-(2-ethylsulphonyl)-imidazo[1,2-a]pyridine-3-sulphonamide (sulfosulfuron), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), methyl 2-difluoromethyl-5-(4,5-dihydro-thiazol-2-yl)-4-(2-methyl-propyl)-6-trifluoromethyl-pyridine-3-carboxylate (thiazopyr), 6-(6,7-dihydro-6,6-dimethyl-3H,5H-pyrrolo[2,1-c]-1,2,4-thiadiazol-3-ylideneamino)-7-fluoro-4-(2-propinyl)-2H-1,4-benzoxazin- 3(4H)-one (thidiazimin), N-(4-methoxy-6-methyl-1,3,5-triazin-2-yl)-N'-(2-methoxy-carbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl)diisopropylcarbamothioate (triallate), N-(4-methoxy-6-methyl-1,3,5-triazin-2-yl)-N'-[2-(2-chloro-ethoxy)-phenylsulphonyl-urea] (triasulfuron), N-methyl-N-(4-methoxy-6-methyl-1,3,5-triazin-2-yl)-N'-(2-methoxycarbonyl-phenylsulphonyl)-urea (tribenuron-methyl), (3,5,6-trichloro)-pyridin-2-yl-oxy-acetic acid (triclopyr), 2-(3,5-dichloro-phenyl)-2-(2,2,2-trichloro-ethyl)-oxiane (tridiphane), N-[[(4,6-dimethoxy-2-pyrimidinyl)-amino]-carbonyl]-3-(2,2,2-trifluoro-ethoxy)-2-pyridinesulphonamide sodium salt (trifloxysulfuron), 1-amino-2,6-dinitro-N,N-dipropyl-4-trifluoromethyl-benzene (trifluralin), N-[4-dimethylamino-6-(2,2,2-trifluoro-ethoxy)-1,3,5-triazin-2-yl]-N'-(2-methoxycarbonyl-phenyl-sulphonyl)-urea (triflusulfuron-methyl), N-(4-methoxy-6-trifluoromethoxy-1,3,5-triazin-2-yl)-N'-(2-trifluoromethyl-phenylsulphonyl)-urea (tritosulfuron), N-[[(4,6-dimethoxy-2-pyrimidinyl)-amino]-carbonyl]-3-(N-methyl-N-methylsulphonyl-amino)-2-pyridinesulphonamide, 4-[4,5-dihydro-4-methyl-5-oxo-(3-trifluoromethyl)-1H-1,2,4-triazol-1-yl]-2-[(ethylsulphonyl)amino]-5-fluoro-benzenecarbothioamide, 4-dichloroacetyl-1-oxa-4-aza-spiro[4,5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazine (benoxacor), 1-methyl-hexyl 5-chloro-quinoxalin-8-oxy-acetate (cloquintocet-mexyl), α-(cyano-methoximino)-phenylacetonitrile (cyometrinil), 2,4-dichlorophenoxy-acetic acid (2,4-D), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), N-(4-methyl-phenyl)-N'-(1-methyl-1-phenyl-ethyl)-urea (dymron), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), (4-chloro-2-methyl-phenoxy)-acetic acid (MCPA), (±)-2-(4-chloro-2-methylphenoxy)propanoic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalic anhydride, α-(1,3-dioxolan-2-yl-methoximino)-phenylacetonitrile (oxabeninil), 2,2-dichloro-N-(1,3-dioxolan-2-yl-methyl)-N-(2-propenyl)-acetamide (PPG-1292), 3-dichloroacetyl-2,2,5-trimethyl-oxazolidine (R-29148), N-cyclopropyl-4-[[(2-methoxy-5-methyl-benzoyl)-amino]-sulphonyl]-benzamide, N-[(4-methylaminocarbonylamino)-phenyl]-sulphonyl-2-methoxy-benzamide.

In one embodiment of the present invention, the herbicidally active compound is one or more selected from among 2,4-D, bensulfuron, bentazone, bispyibac-sodium, bromoxynil, cafenstrole, chloridazon, clethodim, clodinafop, dicamba, diflufenican, fenoxaprop, florasulam, fluazifop, fluefenacet, fluroxypyr, glufosinate, glyphosate, haloxyfop, iodosulfuron, isoproturon, isoxaflutole, MCPA, MCPB, mecoprop, mesosulfuron, metamifop, metsulfuron, picloram, pinoxaden, propanil, pyrazosulfuron, quinchlorac, tralkoxydim, triclopyr, trifloxysulfuron, acetochlor, alachlor, amicarbazone, atrazine, bromacil, carfentrazone-ethyl, chlorimuron-ethyl, clodinafop-propargyl, cyanazine, diclosulam, dimethenamid, S-dimethenamid, diuron, EPTC, fenoxaprop-(P)-ethyl, fentrazamid, flucarbazone-sodium, flufenacet, flurmetsulam, glufosinate-ammonium, glyphosate-isopropylammonium, imazamox, imazaquin, imazethapyr, isoxaflutole, mesotrione, metolachlor, S-metolachlor, metosulam, metribuzin, nicosulfuron, norflurazon, pendimethalin, propoxycarbazone-sodium, rimsulfuron, simazin, sulfometuron-methyl, sulcotrion, sulfentrazone, sulfosate, terbuthylazine, thifensulfuron-methyl, trifluralin, 4-[4,5-dihydro-4-methyl-5-oxo-(3-trifluoromethyl)-1H-1,2, 4-triazol-1-yl]-2-[(ethylsulfonyl)amino]-5-fluoro-benzenecarbothioamide, 1-methyl-hexyl 5-chloro-quinoxalin-8-oxy-acetate (cloquintocet-mexyl), ethyl 4,5-dihydro-5,5- diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl), 4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazine (benoxacor), 3-dichloroacetyl-5-(2-furanyl)-2,2-dimethyl-oxazolidine (furilazole, MON-13900), and 3-dichloroacetyl-2,2,5-trimethyl-oxazolidine (R-29148).

In one embodiment of the present invention, the herbicidal composition further comprises a solid or liquid diluent and surface-active agent. In one embodiment of the present invention, the herbicidally active compound is contained in an amount of 0.01-1,000 parts by weight based on 1 part by weight of the uracil compound represented by formula 1. In another embodiment, the herbicidally active compound is contained in an amount of 0.02-500 parts by weight based on 1 part by weight of the uracil compound represented by formula 1. In still another embodiment, the herbicidally active compound is contained in an amount of 0.05-100 parts by weight based on 1 part by weight of the uracil compound represented by formula 1. In one embodiment of the present invention, said diluent or surface-active agent is contained in an amount of 0.1-99.9 wt % based on the total weight of the composition. In one embodiment of the present invention, the herbicidal composition is in the form of wettable powder, suspensions, emulsifible concentrates, emulsions, microemulsions, soluble concentrates, dispersible concentrates, water dispersible granules, granules, powder, suspension concentrates, water floating granules, or tablets. The active ingredients further include at least one of acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors, and other known herbicides. In one embodiment of the present invention, the herbicidal composition is nonselective. In one embodiment of the present invention, the herbicidal composition is used in dhy-field farming or paddy field farming, and in another embodiment of the present invention, the herbicidal composition is used in paddy field farming.

Agrochemical formulations contain the herbicidal composition of the present invention in an amount of 0.1-95 wt %, and preferably 0.5-90 wt %.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

The surface-active agent that is used in the present invention is an amphiphilic material having high surfactant activity and containing both hydrophilic and lipophilic molecules. It has excellent cleansing, dispersing, emulsifying, solubilizing, wetting, stetilizing, foaming and penetrating abilities, and thus acts to wet, disintegrate, disperse and emulsify the active ingredients so that the effects of the active ingredients are effectively exhibited. The surface-active agent may be one or a mixture of two or more selected from among anionic surface-active agents, including a sodium or calcium salt of a sulfonate, such as alkyl($C_8$-$C_{12}$) benzene sulfonate, alkyl($C_3$-$C_6$)naphthalene sulfonate, dialkyl($C_3$-$C_6$)naphthalene sulfonate, dialkyl($C_8$-$C_{12}$)sulfosuccinate, lignin sulfonate, naphthalene sulfosuccinate formalin concentrates, alkyl($C_8$-$C_{12}$)naphthalene sulfonate formalin concentrates, or polyoxyethylenealkyl($C_8$-$C_{12}$)phenyl sulfonate, a sodium or calcium salt of a sulfate, such as alkyl($C_8$-$C_{12}$)sulfate, polyoxyethylenealkyl($C_8$-$C_{12}$)sulfate, or polyoxyethylenealkyl($C_8$-$C_{12}$)phenyl sulfate, or a sodium or calcium salt of a succinate, such as polyoxyalkylene succinate, and nonionic surface-active agents, such as polyoxyethylenealkyl($C_8$-$C_{12}$)ether, polyoxyethylenealkyl($C_8$-$C_{12}$)phenyl ether, or polyoxyethylenealkyl($C_8$-$C_{12}$)phenyl polymers.

The diluent that is used in the present invention may be either a solid diluent or a liquid diluent. For a solid diluent, one having a high water-absorbing ability is particularly preferably used to prepare wettable powder. For a liquid diluent, one that is stable without phase separation from a solvent even at 0° C. is preferred. Examples of the liquid diluent that may be used in the present invention include water, toluene, xylene, petroleum ether, vegetable oil, acetone, methyl ethyl ketone, cyclohexanone, acid anhydride, acetonitrile, acetophenone, amyl acetate, 2-butanone, butylene carbonate, chlorobenzene, cyclohexane, cyclohexanol, alkyl ester of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, .alpha.-pinene, D-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG), propionic acid, propyl lactate, propylene carbonate, propylene glycol, propylene glycol methyl ether, p-xylene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol and high-molecular-weight alcohol, e.g., amyl alcohol, tetrahydrofurfuryl alcohol, hexanol, octanol, ethylene glycol, propylene glycol and glycerol, N-methyl-2-pyrrolidone, or the like. The solid diluent may be talc, titanium dioxide, agalmatolite clay, silica, attapulgite clay, diatomite, limestone, calcium carbonate, bentonite, calcium montmorillonite, cottonseed hull, wheatmeal, soybean flour, pumice, wood flour, nutshell, lignin, and the like.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulfoxide, and water.

Suitable solid carriers are, for example, ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are, for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam-formers are, for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates. Suitable dispersants are, for example, lignin-sulfite waste liquors and methylcellulose. Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils. It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

A safener that may be used in the present invention is one or more selected from the group consisting of benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil.

The above-described herbicidally active compounds include a number of known safeners or antidotes capable of antagonizing the damaging effect of herbicide on crop plants. It is known that 2,4-dichlorophenoxy-acetic acid (2,4-D) and its derivatives, (4-chloro-2-methylphenoxy)acetic acid (MCPA), (±)-2-(4-chloro-2-methylphenoxy)propanoic acid (mecoprop) are herbicidally active compounds that act as safeners or antidotes. The compounds that act as safeners or antidotes are herbicidally active compounds that may be included in the herbicidal composition of the present invention, and these compounds neutralize the damaging effect of compounds on the crop plants virtually completely without adversely affecting the herbicidal activity against weeds. At least one of said safeners or antidotes may be used in a mixture with the herbicidal composition of the present invention.

As used herein, the term "dry-field farming" refers to cultivating field crops, including, but not limited to, potatoes, sweet potatoes, carrots, Chinese cabbages, radishes, corn, watermelons, lettuce, sesame or perilla leaves, beans, Perilla japonica, sesame, red pepper, cucumbers, eggplants, and kale. As used herein, the term "paddy field farming" means farming that is performed by water irrigation, and typical examples thereof include rice farming. As used herein, the term "nonselective herbicide" refers to one that kills all plants without distinction between crops and weeds. Specifically, "non-selective herbicide" refers to one that can kill all plants which grow not only in rice fields and gardens, but also places in which crops are not cultivated, including fallow areas, the bank around a rice field, and a furrow.

The herbicidal composition of the present invention can be used in a mixture with other known herbicides or a formulation thereof. The active compounds in the herbicidal composition of the present invention are applied in the form of ready mixes. However, the active compounds can also be formulated individually and mixed upon use, i.e., applied in the form of tank mixes. The composition of the present invention may be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Rako Binol") or ammonium salts, for example, ammonium sulfate or ammonium thiocyanate, as further additives.

The herbicidal composition of the present invention can be used as such, in the form of their formulations or in the use forms prepared therefrom by further dilution, such as ready-to-use solutions, suspensions, emulsions, powders, pastes and granules. It is used in the customary manner, for example by watering, spraying, atomizing, dusting or broadcasting.

The herbicidal composition of the present invention may include one or more compounds represented by formula 1 as active ingredients. Moreover, the uracil compound may be a free base of the compound represented by formula 1 or an agrochemically acceptable salt thereof. In addition, because one or more chiral carbons can exist in the molecular structure of the compound represented by formula 1, the definition of the uracil compound of the present invention includes single enantiomers, diasteromers, racemates and the like.

Examples of an agrochemically acceptable salt of the compound represented by formula 1 include metal salts, salts with organic bases, salts with organic acids, salts with basic or acidic amino acids, and the like. Metal salts include, for example, alkali metal salts, such as sodium or potassium salts, alkaline earth metal salts, such as magnesium or barium salts, aluminum salts, and the like. Salts with organic bases include, for example, salts with trimethylamine, triethylamine, pyridine, picoline, 2,6- lutidine, ethanolamine, diethanolamine, triethanolamine, cyclohexylamine, dicyclohexylamine, N,N-dibenzylethylenediamine and the like. Examples of salts with inorganic acids include salts with hydrochloric acid, hydrobromic acid, nitric acid, sulfuric acid, phosphoric acid, etc. Examples of salts with organic acids include salts with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc. Examples of salts with basic amino acids include salts with arginine, lysine, ornithine, etc. Examples of salts with acidic amino acids include salts with aspartic acid, glutamic acid, etc.

According to the invention, it is possible to treat all plants and parts of plants with the herbicidal composition of the present invention. The term plants should be understood here to mean all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant vareties which can or cannot be protected by varietal property rights. Parts of plants are to be understood as meaning all above-ground and below-ground parts and organs of plants, such as shoots, leaves, flowers and roots, examples which may be mentioned being leaves, needles, stems, trunks, flowers, fruit-bodies, fruits and seeds and also roots, tubers and rhizomes. Parts of plants also include vegetative and generative propagation material, for example seedlings, tubers, rhizomes, cuttings and seeds.

The treatment of plants and parts of plants with the herbicidal composition of the present invention is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating. Among the plants obtained by biotechnological or genetic engineering methods or by combinations of these methods, emphasis is given to those plants which tolerate the so-called 4HPPD, EPSP and/or PPO inhibitors, such as, for example, Acuron plants.

The herbicidal composition according to the invention can be applied to the following plants. However, the use of the active compound combinations according to the invention is in no way restricted to these genera, but also extends in the same manner to other plants:

Dicotyledonous weeds: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola,* and *Xanthium;*

Dicotyledonous crops: *Arachis, Brassica, Cucumis, Cucurbita, Helianthus, Daucus, Gossypium, Ipomoea, Lactuca, Linum, Lycopersicon, Nicotiana, Phaseolus, Pisum, Solanum* and *Vicia;*

Monocdtyledonous weeds: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria,* and *Sorghum;*

Monocotyledonous crops: *Allium, Ananas, Asparagus, Avena, Hordeum, Oryza, Panicum, Saccharum, Secale, Sorghum, Triticale, Triticum,* and *Zea.*

The herbicidal compositions according to the invention can be used both in conventional methods of cultivation (strip cultivation with suitable strip width) and in plantation cultivation (e.g., vines, fruit, citrus), as well as in industrial plants and track systems, on roads and squares, but also to handle stubble and in the minimum-tillage method. They are also suitable as burners (for killing foliage, e.g. in potatoes) or as defoliants (e.g. in cotton).

They are also suitable for use on fallow areas. Other areas of use are in tree nurseries, forests, grasslands, and in the cultivation of ornamental plants. The herbicidal composition according to the invention can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

The herbicidal composition according to the invention can be applied before and after the plants have emerged, that is to say pre-emergence and post-emergence. It can also be incorporated into the soil before sowing. The good herbicidal activity of the herbicidal composition of the present invention can be seen from the examples which follow. While the individual active compounds show weak points regarding the herbicidal activity, the combinations, without exception, display a very good activity against weeds, which exceeds a simple additive effect. A synergistic effect in herbicides is always present when the herbicidal activity of the active combination exceeds the activity of the active compounds when applied individually.

The expected activity for a given combination of two herbicides can be calculated as shown in the following equation 1 (COLBY, S. R., "Calculating synergistic and antagonistic responses of herbicide combinations", Weeds 15, pages 20-22, 1967):

Equation 1

$$E=X+Y-(X\times Y/100)$$

In Equation 1,

X is % damage by uracil compound (a) of formula 1 at the rate of application of p kg/ha; Y is % damage by conventional herbicidal compound (b) at the rate of application of q kg/ha; and E is the expected damage caused by compounds (a) and (b) at a rate of application of p and q kg/ha.

EXAMPLES

Hereinafter, the present invention will be described further with reference to examples. It is to be understood, however, that these examples are for illustrative purposes only and are not intended to limit the scope of the present invention.

In the following examples, the compounds disclosed in Korean Patent No. 1,103,840 were mixed with other herbicidally active compounds, and the effects thereof were examined.

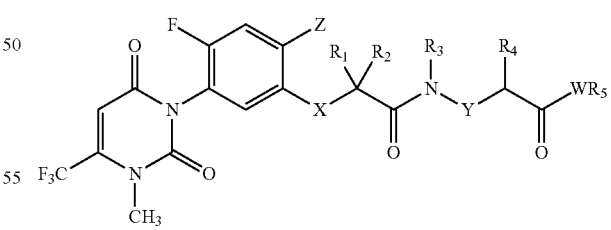

Formula 1

In Formula 1, $R^1$ and $R^2$ are the same or different and represent a hydrogen atom or a $C_1$-$C_6$ alkyl group; $R^3$ represents a hydrogen atom, a hydroxyl group, a $C_1$-$C_6$ alkyl group, a $C_2$-$C_6$ alkenyl group, a $C_2$-$C_6$ alkynyl group, a $C_1$-$C_8$ alkoxy group, a $C_1$-$C_6$ haloalkyl group, a $C_2$-$C_6$ haloalkenyl group, a $C_1$-$C_6$ alkoxy $C_1$-$C_6$ alkyl group, or a $C_6$-$C_{10}$ aryl $C_1$-$C_6$ alkoxy group; $R^4$ represents a hydrogen atom, a $C_1$-$C_6$ alkyl group, a $C_1$-$C_6$ haloalkyl group, or a $C_1$-$C_6$ alkoxycarbonyl $C_1$-$C_6$ alkyl group; $R^5$ represents a hydrogen atom, a $C_1$-$C_6$ alkyl group, a $C_1$-$C_6$ alkoxy group, a $C_2$-$C_6$ haloalkyl group, a $C_2$-$C_6$ alkenyl group, a $C_2$-$C_6$ haloalkenyl group, a $C_2$-$C_6$ alkynyl group, a $C_1$-$C_6$ alkoxycarbonyl group, a $C_1$-$C_6$ alkyl group, a $C_6$-$C_{10}$ aryl $C_1$-$C_6$ alkyl group, or a $C_6$-$C_{10}$ aryl $C_1$-$C_6$ alkoxy group; X represents O, S, SO, $SO_2$, NH, or N($C_1$-$C_6$ alkyl); Y represents a $C_1$-$C_6$ alkylene group or a $C_1$-$C_6$ haloalkylene group; W represents O, S, NH, or N($C_1$-$C_6$ alkyl); and Z represents a halogen atom, a cyano group, $CONH_2$, or $CSNH_2$.

Preferably, the uracil compound represented by formula 1 is a uracil compound wherein $R^1$ and $R^2$ are the same or different and represent a hydrogen atom or a methyl group; $R^3$ represents a hydrogen atom, a hydroxyl group, a methyl group, a methoxy group or a benzyloxy group; $R^4$ represents a hydrogen atom or a methyl group; $R^5$ represents a hydrogen atom, a methyl group, an ethyl group, a n-propyl group, a n-butyl group, a methoxy group, an allyl group, a propargyl group, a benzyl group, a benzyloxy group, or a methoxycarbonylmethyl group; X represents O, S, $SO_2$, or NH; Y represents $CH_2$, $CH(CH_3)$, $CH_2CH_2$, $CH_2CH_2CH_2$, or $CH(CH_2F)$; W represents O, or NH; and Z represents a chlorine atom, a cyano group, or $CSNH_2$.

More preferably, the uracil compound represented by formula 1 is a uracil compound wherein $R^1$ and $R^2$ are the same or different and represent a hydrogen atom or a methyl group; $R^3$ represents a hydrogen atom, a hydroxyl group, a methyl group, or a methoxy group; $R^4$ represents a hydrogen atom; $R^5$ represents a hydrogen atom, a methyl group, an ethyl group, a n-butyl group, an allyl group, a propargyl group, or $CH_2CO_2CH_3$; X represents O, S, or NH; Y represents $CH_2$, $CH_2CH_2$, or $CH(CH_2F)$; W represents O; and Z represents a chlorine atom.

Among the compounds represented by formula 1 according to the present invention, particularly preferable compounds are as follows:

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (compound 1);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}methoxyamino]propionic acid methyl ester (compound 4);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}benzyloxyamino]propionic acid methyl ester (Compound 5);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}hydroxyamino]propionic acid methyl ester (compound 6);

3-[{2-[2-chloro-5-(3,6-dihydro-3-methyl-2,6-dioxo-4-trifluoromethyl-1(2H)-pyrimidinyl)-4-fluoropphenoxy]-1-oxopropyl}amino]-4-fluorobutyric acid methyl ester (compound 8);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]butyric acid methyl ester (compound 9);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]-2-methylpropionic acid methyl ester (compound 10);

4-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]butyric acid methyl ester (compound 11);

5-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]pentanoic acid methyl ester (compound 12);

3-[{2-[2-chloro-5-(3,6-dihydro-3-methyl-2,6-dioxo-4-trifluoromethyl-1(2H)-pyrimidinyl)-4-fluorophenoxy]-1-oxoethyl}amino]propionic acid methyl ester (compound 13);

3-[{2-[2-chloro-5-(3,6-dihydro-3-methyl-2,6-dioxo-4-trifluoromethyl-1(2H)-pyrimidinyl)-4-fluorophenylamino]-1-oxopropyl}amino]propionic acid methyl ester (compound 15); 3-[{2-[2-chloro-5-(3,6-dihydro-3-methyl-2,6-dioxo-4-trifluoromethyl-1(2H)-pyrimidinyl)-4-fluorophenoxy]-1-oxoethyl}methylamino]propionic acid methyl ester (compound 16);

3-[{2-[2-chloro-5-(3,6-dihydro-3-methyl-2,6-dioxo-4-trifluoromethyl-1(2H)-pyrimidinyl)-4-fluorophenoxy]-1-oxoisopropyl}amino]propionic acid methyl ester (compound 18);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid benzyl ester (compound 20);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid n-propyl ester (compound 21);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionyloxy acetic acid methyl ester (compound 22);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid n-butyl ester (compound 23);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid ethyl ester (compound 24);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid allyl ester (compound 25);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid propargyl ester (compound 26);

4-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]butyric acid ethyl ester (compound 28);

3-[{2-[2-chloro-5-(3,6-dihydro-3-methyl-2,6-dioxo-4-trifluoromethyl-1(2H)-pyrimidinyl)-4-fluorophenylthio]-1-oxopropyl}amino]propionic acid methyl ester (compound 36);

3-[{2-[2-cyano-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (compound 46);

3-[{2-[2-aminothiocarbonyl-5-(3,6-dihydro-3-methyl-2,6-dioxo-4-trifluoromethyl-1(2H)-pyrimidinyl)-4-fluorophenoxy]-1-oxopropyl}amino]propiponic acid methyl ester (compound 52); and 3-[{2-[2-chloro-5-(3,6-dihydro-3-methyl-2,6-dioxo-4-trifluoromethyl-1(2H)-pyrimidinyl)-4-fluorophenylsulfonyl]-1-oxopropyl}amino]propionic acid methyl ester (compound 61).

The chemical structures of the above-described uracil compounds are summarized in Table 1 below.

TABLE 1

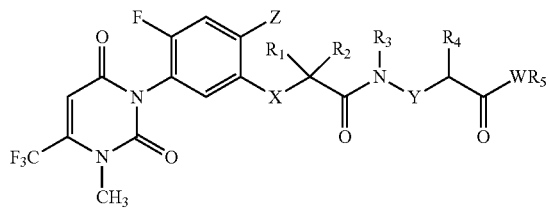

| R¹ | R² | R³ | R⁴ | R⁵ | X | Y | W | Z |
|---|---|---|---|---|---|---|---|---|
| Me | H | H | H | Me | O | CH$_2$ | O | Cl |
| Me | H | H | Me | Me | O | CH$_2$ | O | Cl |
| Me | H | H | H | H | O | CH$_2$ | O | Cl |
| Me | H | OMe | H | Me | O | CH$_2$ | O | Cl |
| Me | H | OBn | H | Me | O | CH$_2$ | O | Cl |
| Me | H | OH | H | Me | O | CH$_2$ | O | Cl |
| Me | H | H | H | Pr | O | CHMe | O | Cl |
| Me | H | H | H | Et | O | CHCH$_2$F | O | Cl |
| HMe | H | H | H | Me | O | CHMe | O | Cl |
| Me | H | H | Me | Me | O | CH$_2$ | O | Cl |
| HMe | H | H | H | Me | O | CH$_2$CH$_2$ | O | Cl |
| HMe | H | H | H | Me | O | CH$_2$CH$_2$CH$_2$ | O | Cl |
| H | H | H | H | Me | O | CH$_2$ | O | Cl |
| H | H | H | H | H | O | CH$_2$ | O | Cl |
| HMe | H | H | H | Me | NH | CH$_2$ | O | Cl |
| H | H | Me | H | Me | O | CH$_2$ | O | Cl |
| HMe | H | H | H | n-Pr | O | CH$_2$ | O | Cl |
| HMe | Me | H | H | Me | O | CH$_2$ | O | Cl |
| HMe | Me | H | H | Et | O | CH$_2$ | O | Cl |
| HMe | H | H | H | Bn | O | CH$_2$ | O | Cl |
| HMe | H | H | H | n-Pr | O | CH$_2$ | O | Cl |
| HMe | H | H | H | CH$_2$CO$_2$Me | O | CH$_2$ | O | Cl |
| HMe | H | H | H | n-Bu | O | CH$_2$ | O | Cl |
| HMe | H | H | H | Et | O | CH$_2$ | O | Cl |
| HMe | H | H | H | Allyl | O | CH$_2$ | O | Cl |
| HMe | H | H | H | Propargyl | O | CH$_2$ | O | Cl |
| HMe | Me | H | H | Allyl | O | NH | O | Cl |
| HMe | H | H | H | Et | O | CH$_2$CH$_2$ | O | Cl |
| HMe | H | Me | H | Me | O | CH$_2$ | O | Cl |
| HMe | H | Me | H | H | O | CH$_2$ | O | Cl |
| HMe | Me | H | H | H | O | CH$_2$ | O | Cl |
| H | H | H | H | Et | O | CH$_2$ | O | Cl |
| Me | H | H | Me | Me | NH | CHMe | O | Cl |
| HMe | H | CH$_2$F | H | Me | O | CH$_2$ | O | Cl |
| HMe | H | Allyl | H | Me | O | CH$_2$ | O | Cl |
| HMe | H | H | H | Me | S | CH$_2$ | O | Cl |
| HMe | H | H | H | Et | S | CH$_2$ | O | Cl |
| HMe | H | OMe | H | Me | S | CH$_2$ | O | Cl |
| HMe | H | H | H | Me | S | CHMe | O | Cl |
| Me | H | H | Me | Et | S | CHMe | O | Cl |
| HMe | H | H | H | Et | O | CHMe | O | Cl |
| HMe | H | H | H | Me | NH | CH$_2$ | O | Cl |
| HMe | H | Me | H | Me | NH | CH$_2$ | O | Cl |
| HMe | H | OMe | H | Me | NH | CH$_2$ | O | Cl |
| HMe | H | OMe | H | Et | O | CH$_2$ | O | Cl |
| HMe | H | H | H | Me | O | CH$_2$ | O | CN |
| HMe | H | H | H | Et | O | CH$_2$ | O | CN |
| HMe | H | H | H | n-pr | O | CH$_2$ | O | CN |
| HMe | H | H | H | Me | O | CH$_2$ | O | CONH$_2$ |
| HMe | H | H | H | Et | O | CH$_2$ | O | CONH$_2$ |
| HMe | H | H | H | n-pr | O | CH$_2$ | O | CONH$_2$ |
| HMe | H | H | H | Me | O | CH$_2$ | O | CSNH$_2$ |
| HMe | H | H | H | Et | O | CH$_2$ | O | CSNH$_2$ |
| HMe | H | H | H | n-pr | O | CH$_2$ | O | CSNH$_2$ |
| HMe | H | H | H | Me | O | CH$_2$ | NH | Cl |
| HMe | H | H | H | Et | O | CH$_2$ | NH | Cl |

TABLE 1-continued

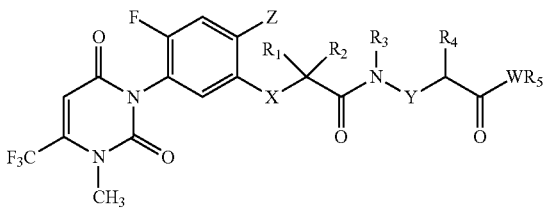

| R¹ | R² | R³ | R⁴ | R⁵ | X | Y | W | Z |
|---|---|---|---|---|---|---|---|---|
| HMe | H | H | H | OMe | O | CH$_2$ | NH | Cl |
| HMe | H | H | H | OH | O | CH$_2$ | NH | Cl |
| HMe | H | H | H | OBn | O | CH$_2$ | NH | Cl |
| HMe | H | H | H | Me | SO | CH$_2$ | O | Cl |
| HMe | H | H | H | Me | SO$_2$ | CH$_2$ | O | Cl |

Me: methyl group; Et: ethyl group; n-Pr: propyl group; Bu: butyl group; Bn: benzyl group.

To test herbicidal activities, (1) in the case of non-selective herbicidal compositions, weeds at the growth stage (30-40 cm) in fallow areas and orchards were treated with compositions containing the uracil compounds and herbicidally active compounds. (2) In the case of dry-field farming, weeds at the initial growth state (5 cm or less) in wheat and corn fields weeds were treated with compositions containing the uracil compounds and herbicidally active compounds. (3) In the case of paddy field farming weeds in rice fields were treated with compositions containing the uracil compounds and herbicidally active compounds at 15 days after rice transplantation.

Herbicidal activities were visually evaluated by comparing the mortality of the plants with untreated control groups 20 days after treatment with the compositions.

Meanwhile, if the actual damage exceeds the calculated value, then the activity of the combination is superadditive. The expected activity for a given combination of two herbicides can be calculated using equation 1 above.

Example 1

Nonselective Herbicidal Composition

Weeds at the weed growth stage (30-40 cm) in fallow areas and orchards were treated with nonselective herbicidal compositions containing the uracil compounds and herbicidally active compounds.

Experimental Example

Tables 2 to 29 below show the plant mortalities (herbicidal activities) obtained when *Echinochloa crus*, *Digitaria sanguinalis*, *Abutilon theophrasti*, *Aeschynomene indica* and *Xanthium spinosum* were treated with the indicated amounts of uracil compounds, nonselective herbicides, and uracil compound/herbicide mixtures. When the measured values are higher than the calculated values, the test materials have significant herbicidal activities. The left column of two columns for each grass in the following tables indicates measured mortality values, and the right column indicates calculated mortality values.

TABLE 2

| | | Data (measured value/calculated value) | | | | | | | | |
|---|---|---|---|---|---|---|---|---|---|---|
| Component | g/ha | *Echinochloa crus* | | *Digitaria sanguinalis* | | *Abutilon theophrasti* | | *Aeschynomene indica* | | *Xanthium spinosum* | |
| Compound 1 | 4 | 0 | — | 0 | — | 17 | — | 18 | — | 11 | — |
| Compound 1 | 8 | 5 | — | 5 | — | 45 | — | 45 | — | 39 | — |

TABLE 2-continued

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 1 | 16 | 17 | — | 20 | — | 60 | — | 60 | — | 52 | — |
| Glyphosate | 150 | 12 | — | 8 | — | 8 | — | 9 | — | 11 | — |
| Glyphosate | 300 | 23 | — | 18 | — | 27 | — | 22 | — | 30 | — |
| Glyphosate | 600 | 48 | — | 46 | — | 59 | — | 47 | — | 64 | — |
| Compound 1 + Glyphosate | 4 + 600 | 53 | 48 | 49 | 46 | 70 | 66 | 63 | 57 | 78 | 68 |
| Compound 1 + Glyphosate | 8 + 300 | 50 | 27 | 44 | 22 | 95 | 60 | 91 | 57 | 88 | 57 |
| Compound 1 + Glyphosate | 16 + 150 | 36 | 27 | 36 | 26 | 68 | 63 | 72 | 64 | 67 | 57 |

TABLE 3

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 1 | 4 | 0 | — | 0 | — | 17 | — | 18 | — | 11 | — |
| Compound 1 | 8 | 5 | — | 5 | — | 45 | — | 45 | — | 39 | — |
| Compound 1 | 16 | 17 | — | 20 | — | 60 | — | 60 | — | 52 | — |
| Glufosinate | 75 | 15 | — | 11 | — | 7 | — | 5 | — | 13 | — |
| Glufosinate | 150 | 29 | — | 27 | — | 25 | — | 18 | — | 25 | — |
| Glufosinate | 300 | 60 | — | 57 | — | 49 | — | 46 | — | 56 | — |
| Compound 1 + Glufosinate | 4 + 300 | 64 | 60 | 66 | 57 | 67 | 58 | 60 | 56 | 64 | 61 |
| Compound 1 + Glufosinate | 8 + 150 | 56 | 33 | 53 | 30 | 89 | 58 | 86 | 55 | 84 | 54 |
| Compound 1 + Glufosinate | 16 + 75 | 39 | 29 | 36 | 29 | 73 | 63 | 70 | 62 | 66 | 58 |

TABLE 4

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 11 | — | 26 | — | 21 | — |
| Compound 36 | 8 | 5 | — | 5 | — | 38 | — | 52 | — | 42 | — |
| Compound 36 | 16 | 10 | — | 16 | — | 51 | — | 69 | — | 56 | — |
| Glyphosate | 150 | 12 | — | 8 | — | 8 | — | 9 | — | 11 | — |
| Glyphosate | 300 | 23 | — | 18 | — | 27 | — | 22 | — | 30 | — |
| Glyphosate | 600 | 48 | — | 46 | — | 59 | — | 47 | — | 64 | — |
| Compound 36 + Glyphosate | 4 + 600 | 57 | 48 | 56 | 46 | 68 | 64 | 66 | 61 | 76 | 72 |
| Compound 36 + Glyphosate | 8 + 300 | 48 | 27 | 44 | 22 | 87 | 54 | 94 | 62 | 92 | 59 |
| Compound 36 + Glyphosate | 16 + 150 | 25 | 20 | 29 | 23 | 63 | 55 | 78 | 72 | 64 | 61 |

TABLE 5

| Component | g/ha | Data (measured value/calculated value) | | | | | | | | | |
|---|---|---|---|---|---|---|---|---|---|---|---|
| | | *Echinochloa crus* | | *Digitaria sanguinalis* | | *Abutilon theophrasti* | | *Aeschynomene indica* | | *Xanthium spinosum* | |
| Compound 36 | 4 | 0 | — | 0 | — | 11 | — | 26 | — | 21 | — |
| Compound 36 | 8 | 5 | — | 5 | — | 38 | — | 52 | — | 42 | — |
| Compound 36 | 16 | 10 | — | 16 | — | 51 | — | 69 | — | 56 | — |
| Glufosinate | 75 | 15 | — | 11 | — | 7 | — | 5 | — | 13 | — |
| Glufosinate | 150 | 29 | — | 27 | — | 25 | — | 18 | — | 25 | — |
| Glufosinate | 300 | 60 | — | 57 | — | 49 | — | 46 | — | 56 | — |
| Compound 36 + Glufosinate | 4 + 300 | 63 | 60 | 66 | 57 | 62 | 55 | 70 | 60 | 71 | 65 |
| Compound 36 + Glufosinate | 8 + 150 | 56 | 33 | 54 | 30 | 84 | 53 | 93 | 61 | 90 | 57 |
| Compound 36 + Glufosinate | 16 + 75 | 26 | 23 | 28 | 25 | 61 | 54 | 81 | 71 | 69 | 62 |

TABLE 6

| Component | g/ha | Data (measured value/calculated value) | | | | | | | | | |
|---|---|---|---|---|---|---|---|---|---|---|---|
| | | *Echinochloa crus* | | *Digitaria sanguinalis* | | *Abutilon theophrasti* | | *Aeschynomene indica* | | *Xanthium spinosum* | |
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Fenoxaprop | 25 | 13 | — | 13 | — | 0 | — | 0 | — | 0 | — |
| Fenoxaprop | 50 | 31 | — | 32 | — | 0 | — | 0 | — | 0 | — |
| Fenoxaprop | 100 | 65 | — | 64 | — | 0 | — | 0 | — | 0 | — |
| Compound 36 + Fenoxaprop | 20 + 100 | 79 | 71 | 79 | 71 | 66 | 58 | 63 | 56 | 57 | 51 |
| Compound 36 + Fenoxaprop | 40 + 50 | 90 | 56 | 95 | 61 | 100 | 100 | 100 | 100 | 100 | 90 |
| Compound 36 + Fenoxaprop | 80 + 25 | 74 | 66 | 80 | 75 | 100 | 100 | 100 | 100 | 100 | 100 |

TABLE 7

| Component | g/ha | Data (measured value/calculated value) | | | | | | | | | |
|---|---|---|---|---|---|---|---|---|---|---|---|
| | | *Echinochloa crus* | | *Digitaria sanguinalis* | | *Abutilon theophrasti* | | *Aeschynomene indica* | | *Xanthium spinosum* | |
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Clodinafop | 7.5 | 12 | — | 10 | — | 0 | — | 0 | — | 0 | — |
| Clodinafop | 15 | 25 | — | 21 | — | 0 | — | 0 | — | 0 | — |
| Clodinafop | 30 | 53 | — | 50 | — | 0 | — | 0 | — | 0 | — |
| Compound 36 + Clodinafop | 20 + 30 | 64 | 61 | 68 | 60 | 61 | 58 | 61 | 56 | 60 | 51 |

TABLE 7-continued

| Component | g/ha | Echinochloa crus (measured/calculated) | | Digitaria sanguinalis (measured/calculated) | | Abutilon theophrasti (measured/calculated) | | Aeschynomene indica (measured/calculated) | | Xanthium spinosum (measured/calculated) | |
|---|---|---|---|---|---|---|---|---|---|---|---|
| Compound 36 + Clodinafop | 40 + 15 | 84 | 52 | 83 | 55 | 100 | 100 | 100 | 100 | 100 | 90 |
| Compound 36 + Clodinafop | 80 + 7.5 | 71 | 66 | 83 | 74 | 100 | 100 | 100 | 100 | 100 | 100 |

TABLE 8

| Component | g/ha | Echinochloa crus (measured/calculated) | | Digitaria sanguinalis (measured/calculated) | | Abutilon theophrasti (measured/calculated) | | Aeschynomene indica (measured/calculated) | | Xanthium spinosum (measured/calculated) | |
|---|---|---|---|---|---|---|---|---|---|---|---|
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Fluazifop | 50 | 10 | — | 9 | — | 0 | — | 0 | — | 0 | — |
| Fluazifop | 100 | 26 | — | 21 | — | 0 | — | 0 | — | 0 | — |
| Fluazifop | 200 | 61 | — | 52 | — | 0 | — | 0 | — | 0 | — |
| Compound 36 + Fluazifop | 20 + 200 | 77 | 68 | 71 | 61 | 68 | 58 | 66 | 56 | 54 | 51 |
| Compound 36 + Fluazifop | 40 + 100 | 83 | 53 | 84 | 55 | 100 | 100 | 100 | 100 | 100 | 90 |
| Compound 36 + Fluazifop | 80 + 50 | 75 | 65 | 82 | 73 | 100 | 100 | 100 | 100 | 100 | 100 |

TABLE 9

| Component | g/ha | Echinochloa crus (measured/calculated) | | Digitaria sanguinalis (measured/calculated) | | Abutilon theophrasti (measured/calculated) | | Aeschynomene indica (measured/calculated) | | Xanthium spinosum (measured/calculated) | |
|---|---|---|---|---|---|---|---|---|---|---|---|
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Haloxyfop | 12.5 | 11 | — | 14 | — | 0 | — | 0 | — | 0 | — |
| Haloxyfop | 25 | 28 | — | 29 | — | 0 | — | 0 | — | 0 | — |
| Haloxyfop | 50 | 58 | — | 57 | — | 0 | — | 0 | — | 0 | — |
| Compound 36 + Haloxyfop | 20 + 50 | 74 | 65 | 72 | 65 | 64 | 58 | 60 | 56 | 54 | 51 |
| Compound 36 + Haloxyfop | 40 + 25 | 88 | 54 | 89 | 59 | 100 | 100 | 100 | 100 | 100 | 90 |
| Compound 36 + Haloxyfop | 80 + 12.5 | 75 | 65 | 85 | 75 | 100 | 100 | 100 | 100 | 100 | 100 |

TABLE 10

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{12}{c}{Data (measured value/calculated value)} | | | | | | | | | | |
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Metamifop | 25 | 11 | — | 11 | — | 0 | — | 0 | — | 0 | — |
| Metamifop | 50 | 26 | — | 23 | — | 0 | — | 0 | — | 0 | — |
| Metamifop | 100 | 57 | — | 48 | — | 0 | — | 0 | — | 0 | — |
| Compound 36 + Metamifop | 20 + 100 | 68 | 64 | 65 | 58 | 67 | 58 | 65 | 56 | 54 | 51 |
| Compound 36 + Metamifop | 40 + 50 | 84 | 53 | 88 | 56 | 100 | 100 | 100 | 100 | 100 | 90 |
| Compound 36 + Metamifop | 80 + 25 | 68 | 65 | 78 | 74 | 100 | 100 | 100 | 100 | 100 | 100 |

TABLE 11

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Pinoxaden | 6.25 | 10 | — | 12 | — | 0 | — | 0 | — | 0 | — |
| Pinoxaden | 12.5 | 29 | — | 26 | — | 0 | — | 0 | — | 0 | — |
| Pinoxaden | 25 | 63 | — | 57 | — | 0 | — | 0 | — | 0 | — |
| Compound 36 + Pinoxaden | 20 + 25 | 72 | 69 | 72 | 65 | 62 | 58 | 62 | 56 | 61 | 51 |
| Compound 36 + Pinoxaden | 40 + 12.5 | 85 | 55 | 90 | 57 | 100 | 100 | 100 | 100 | 100 | 90 |
| Compound 36 + Pinoxaden | 80 + 6.25 | 73 | 65 | 82 | 74 | 100 | 100 | 100 | 100 | 100 | 100 |

TABLE 12

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Clethodim | 25 | 11 | — | 6 | — | 0 | — | 0 | — | 0 | — |
| Clethodim | 50 | 31 | — | 19 | — | 0 | — | 0 | — | 0 | — |
| Clethodim | 100 | 65 | — | 45 | — | 0 | — | 0 | — | 0 | — |

TABLE 12-continued

|  |  | Data (measured value/calculated value) | | | | | | | | |
|---|---|---|---|---|---|---|---|---|---|---|
|  |  | Echinochloa crus | | Digitaria sanguinalis | | Abutilon theophrasti | | Aeschynomene indica | | Xanthium spinosum | |
| Component | g/ha | | | | | | | | | | |
| Compound 36 + Clethodim | 20 + 100 | 80 | 71 | 66 | 56 | 61 | 58 | 62 | 56 | 61 | 51 |
| Compound 36 + Clethodim | 40 + 50 | 88 | 56 | 84 | 53 | 100 | 100 | 100 | 100 | 100 | 90 |
| Compound 36 + Clethodim | 80 + 25 | 69 | 65 | 82 | 73 | 100 | 100 | 100 | 100 | 100 | 100 |

TABLE 13

|  |  | Data (measured value/calculated value) | | | | | | | | |
|---|---|---|---|---|---|---|---|---|---|---|
|  |  | Echinochloa crus | | Digitaria sanguinalis | | Abutilon theophrasti | | Aeschynomene indica | | Xanthium spinosum | |
| Component | g/ha | | | | | | | | | | |
| Compound 36 | 20 | 17 | — | 19 | — | 58 | — | 56 | — | 51 | — |
| Compound 36 | 40 | 37 | — | 43 | — | 100 | — | 100 | — | 90 | — |
| Compound 36 | 80 | 61 | — | 71 | — | 100 | — | 100 | — | 100 | — |
| Tralkoxydim | 25 | 10 | — | 8 | — | 0 | — | 0 | — | 0 | — |
| Tralkoxydim | 50 | 24 | — | 21 | — | 0 | — | 0 | — | 0 | — |
| Tralkoxydim | 100 | 56 | — | 47 | — | 0 | — | 0 | — | 0 | — |
| Compound 36 + Tralkoxydim | 20 + 100 | 69 | 64 | 64 | 57 | 66 | 58 | 66 | 56 | 60 | 51 |
| Compound 36 + Tralkoxydim | 40 + 50 | 80 | 52 | 83 | 54 | 100 | 100 | 100 | 100 | 100 | 90 |
| Compound 36 + Tralkoxydim | 80 + 25 | 69 | 65 | 81 | 73 | 100 | 100 | 100 | 100 | 100 | 100 |

TABLE 14

|  |  | Data (measured value/calculated value) | | | | | | | | |
|---|---|---|---|---|---|---|---|---|---|---|
|  |  | Echinochloa crus | | Digitaria sanguinalis | | Abutilon theophrasti | | Aeschynomene indica | | Xanthium spinosum | |
| Component | g/ha | | | | | | | | | | |
| Compound 36 | 4 | 0 | — | 0 | — | 15 | — | 19 | — | 24 | — |
| Compound 36 | 8 | 5 | — | 5 | — | 35 | — | 46 | — | 59 | — |
| Compound 36 | 16 | 12 | — | 15 | — | 47 | — | 61 | — | 79 | — |
| Imazethapyr | 25 | 11 | — | 11 | — | 9 | — | 11 | — | 9 | — |
| Imazethapyr | 50 | 26 | — | 26 | — | 24 | — | 25 | — | 20 | — |
| Imazethapyr | 100 | 53 | — | 62 | — | 58 | — | 54 | — | 47 | — |
| Compound 36 + Imazethapyr | 4 + 100 | 56 | 53 | 65 | 62 | 67 | 64 | 72 | 63 | 68 | 60 |
| Compound 36 + Imazethapyr | 8 + 50 | 51 | 29 | 52 | 30 | 78 | 51 | 95 | 60 | 91 | 67 |
| Compound 36 + Imazethapyr | 16 + 25 | 31 | 21 | 28 | 24 | 55 | 51 | 69 | 65 | 86 | 81 |

TABLE 15

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Compound 36 | 4 | 0 | — | 0 | — | 15 | — | 19 | — | 24 | — |
| Compound 36 | 8 | 5 | — | 5 | — | 35 | — | 46 | — | 59 | — |
| Compound 36 | 16 | 12 | — | 15 | — | 47 | — | 61 | — | 79 | — |
| Trifloxysulfuron | 1.25 | 8 | — | 8 | — | 12 | — | 9 | — | 13 | — |
| Trifloxysulfuron | 2.5 | 24 | — | 26 | — | 28 | — | 25 | — | 30 | — |
| Trifloxysulfuron | 5 | 56 | — | 51 | — | 61 | — | 58 | — | 62 | — |
| Compound 36 + Trifloxysulfuron | 4 + 5 | 59 | 56 | 55 | 51 | 75 | 67 | 73 | 66 | 75 | 71 |
| Compound 36 + Trifloxysulfuron | 8 + 2.5 | 50 | 28 | 54 | 29 | 83 | 53 | 91 | 60 | 96 | 71 |
| Compound 36 + Trifloxysulfuron | 16 + 1.25 | 26 | 19 | 29 | 22 | 60 | 53 | 69 | 65 | 90 | 81 |

TABLE 16

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Compound 36 | 4 | 0 | — | 0 | — | 15 | — | 19 | — | 24 | — |
| Compound 36 | 8 | 5 | — | 5 | — | 35 | — | 46 | — | 59 | — |
| Compound 36 | 16 | 12 | — | 15 | — | 47 | — | 61 | — | 79 | — |
| Bispyribac-sodium | 7.5 | 6 | — | 8 | — | 16 | — | 6 | — | 10 | — |
| Bispyribac-sodium | 15 | 23 | — | 20 | — | 31 | — | 23 | — | 27 | — |
| Bispyribac-sodium | 30 | 45 | — | 47 | — | 62 | — | 49 | — | 58 | — |
| Compound 36 + Bispyribac-sodium | 4 + 30 | 57 | 45 | 64 | 47 | 75 | 68 | 65 | 59 | 75 | 68 |
| Compound 36 + Bispyribac-sodium | 8 + 15 | 81 | 26 | 81 | 24 | 85 | 55 | 86 | 58 | 95 | 70 |
| Compound 36 + Bispyribac-sodium | 16 + 7.5 | 69 | 18 | 72 | 22 | 63 | 55 | 70 | 64 | 85 | 81 |

TABLE 17

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| 2,4-D | 100 | 0 | — | 0 | — | 7 | — | 7 | — | 10 | — |
| 2,4-D) | 200 | 0 | — | 0 | — | 21 | — | 24 | — | 22 | — |
| 2,4-D) | 400 | 0 | — | 0 | — | 47 | — | 51 | — | 50 | — |
| Compound 36 + 2,4-D | 4 + 400 | 6 | 0 | 3 | 0 | 65 | 52 | 63 | 61 | 67 | 63 |

TABLE 17-continued

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{12}{c}{Data (measured value/calculated value)} | | | | | | | | | | | |
| Compound 36 + 2,4-D | 8 + 200 | 10 | 5 | 15 | 10 | 75 | 44 | 91 | 58 | 95 | 61 |
| Compound 36 + 2,4-D | 16 + 100 | 18 | 10 | 19 | 15 | 60 | 49 | 74 | 67 | 89 | 73 |

TABLE 18

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| Dicamba | 75 | 0 | — | 0 | — | 9 | — | 7 | — | 13 | — |
| Dicamba | 150 | 0 | — | 0 | — | 20 | — | 23 | — | 29 | — |
| Dicamba | 300 | 0 | — | 0 | — | 46 | — | 51 | — | 62 | — |
| Compound 36 + Dicamba | 4 + 300 | 10 | 0 | 7 | 0 | 64 | 51 | 64 | 61 | 75 | 72 |
| Compound 36 + Dicamba | 8 + 150 | 21 | 5 | 22 | 10 | 79 | 44 | 91 | 57 | 90 | 65 |
| Compound 36 + Dicamba | 16 + 75 | 20 | 10 | 21 | 15 | 54 | 50 | 72 | 68 | 84 | 74 |

TABLE 19

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| Picloram | 25 | 0 | — | 0 | — | 9 | — | 9 | — | 9 | — |
| Picloram | 50 | 0 | — | 0 | — | 28 | — | 21 | — | 26 | — |
| Picloram | 100 | 0 | — | 0 | — | 65 | — | 52 | — | 56 | — |
| Compound 36 + Picloram | 4 + 100 | 7 | 0 | 8 | 0 | 77 | 69 | 70 | 62 | 70 | 67 |
| Compound 36 + Picloram | 8 + 50 | 21 | 5 | 22 | 10 | 85 | 49 | 86 | 57 | 90 | 63 |
| Compound 36 + Picloram | 16 + 25 | 18 | 10 | 22 | 15 | 56 | 50 | 71 | 68 | 88 | 73 |

TABLE 20

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| Fluroxypyr | 50 | 0 | — | 0 | — | 9 | — | 13 | — | 7 | — |
| Fluroxypyr | 100 | 0 | — | 0 | — | 26 | — | 27 | — | 23 | — |
| Fluroxypyr | 200 | 0 | — | 0 | — | 53 | — | 63 | — | 54 | — |
| Compound 36 + Fluroxypyr | 4 + 200 | 5 | 0 | 7 | 0 | 69 | 58 | 76 | 70 | 71 | 66 |
| Compound 36 + Fluroxypyr | 8 + 100 | 22 | 5 | 22 | 10 | 82 | 48 | 92 | 60 | 90 | 62 |
| Compound 36 + Fluroxypyr | 16 + 50 | 20 | 10 | 19 | 15 | 55 | 50 | 69 | 70 | 80 | 72 |

TABLE 21

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| Triclopyr | 125 | 0 | — | 0 | — | 11 | — | 9 | — | 13 | — |
| Triclopyr | 250 | 0 | — | 0 | — | 23 | — | 26 | — | 30 | — |
| Triclopyr | 500 | 0 | — | 0 | — | 54 | — | 58 | — | 59 | — |
| Compound 36 + Triclopyr | 4 + 500 | 9 | 0 | 10 | 0 | 67 | 59 | 69 | 66 | 74 | 69 |
| Compound 36 + Triclopyr | 8 + 250 | 22 | 5 | 21 | 10 | 82 | 46 | 85 | 59 | 88 | 65 |
| Compound 36 + Triclopyr | 16 + 125 | 16 | 10 | 19 | 15 | 60 | 51 | 74 | 68 | 80 | 74 |

TABLE 22

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| MCPA | 75 | 0 | — | 0 | — | 11 | — | 11 | — | 8 | — |
| MCPA | 150 | 0 | — | 0 | — | 32 | — | 24 | — | 25 | — |
| MCPA | 300 | 0 | — | 0 | — | 64 | — | 58 | — | 59 | — |

TABLE 22-continued

| Component | g/ha | Echinochloa crus | | Digitaria sanguinalis | | Abutilon theophrasti | | Aeschy- nomene indica | | Xanthium spinosum | |
|---|---|---|---|---|---|---|---|---|---|---|---|
| Compound 36 + MCPA | 4 + 300 | 5 | 0 | 3 | 0 | 76 | 68 | 76 | 66 | 77 | 69 |
| Compound 36 + MCPA | 8 + 150 | 22 | 5 | 22 | 10 | 86 | 52 | 85 | 58 | 88 | 62 |
| Compound 36 + MCPA | 16 + 75 | 15 | 10 | 20 | 15 | 63 | 51 | 69 | 69 | 83 | 72 |

TABLE 23

| Component | g/ha | Echinochloa crus | | Digitaria sanguinalis | | Abutilon theophrasti | | Aeschy- nomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| Mecoprop | 200 | 0 | — | 0 | — | 14 | — | 8 | — | 9 | — |
| Mecoprop | 400 | 0 | — | 0 | — | 29 | — | 24 | — | 19 | — |
| Mecoprop | 800 | 0 | — | 0 | — | 64 | — | 55 | — | 45 | — |
| Compound 36 + Mecoprop | 4 + 800 | 6 | 0 | 4 | 0 | 78 | 68 | 73 | 64 | 64 | 59 |
| Compound 36 + Mecoprop | 8 + 400 | 21 | 5 | 21 | 10 | 83 | 50 | 92 | 58 | 85 | 59 |
| Compound 36 + Mecoprop | 16 + 200 | 19 | 10 | 19 | 15 | 58 | 52 | 69 | 68 | 80 | 73 |

TABLE 24

| Component | g/ha | Echinochloa crus | | Digitaria sanguinalis | | Abutilon theophrasti | | Aeschy- nomene indica | | Xanthium spinosum | |
|---|---|---|---|---|---|---|---|---|---|---|---|
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| Quinclorac | 50 | 13 | — | 6 | — | 9 | — | 10 | — | 11 | — |
| Quinclorac | 100 | 26 | — | 21 | — | 26 | — | 27 | — | 29 | — |
| Quinclorac | 200 | 55 | — | 49 | — | 57 | — | 57 | — | 62 | — |
| Compound 36 + Quinclorac | 4 + 200 | 66 | 55 | 55 | 49 | 70 | 61 | 75 | 66 | 80 | 72 |
| Compound 36 + Quinclorac | 8 + 100 | 55 | 29 | 50 | 28 | 80 | 48 | 88 | 60 | 92 | 65 |
| Compound 36 + Quinclorac | 16 + 50 | 30 | 21 | 35 | 20 | 60 | 50 | 76 | 69 | 82 | 73 |

TABLE 25

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{12}{c}{Data (measured value/calculated value)} | | | | | | | | | | |
| Compound 36 | 4 | 0 | — | 0 | — | 10 | — | 20 | — | 25 | — |
| Compound 36 | 8 | 5 | — | 10 | — | 30 | — | 45 | — | 50 | — |
| Compound 36 | 16 | 10 | — | 15 | — | 45 | — | 65 | — | 70 | — |
| MCPB | 75 | 9 | — | 12 | — | 11 | — | 13 | — | 12 | — |
| MCPB | 150 | 27 | — | 25 | — | 22 | — | 32 | — | 27 | — |
| MCPB | 300 | 57 | — | 56 | — | 52 | — | 64 | — | 58 | — |
| Compound 36 + MCPB | 4 + 300 | 62 | 57 | 59 | 56 | 73 | 57 | 83 | 71 | 75 | 69 |
| Compound 36 + MCPB | 8 + 150 | 55 | 30 | 52 | 33 | 80 | 45 | 88 | 63 | 90 | 64 |
| Compound 36 + MCPB | 16 + 75 | 37 | 18 | 28 | 25 | 80 | 51 | 84 | 70 | 74 | 73 |

TABLE 26

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 27 | — | 28 | — | 20 | — |
| Compound 36 | 8 | 5 | — | 5 | — | 54 | — | 54 | — | 48 | — |
| Compound 36 | 16 | 20 | — | 14 | — | 72 | — | 72 | — | 64 | — |
| Chloridazon | 175 | 13 | — | 14 | — | 14 | — | 11 | — | 7 | — |
| Chloridazon | 350 | 27 | — | 28 | — | 30 | — | 29 | — | 22 | — |
| Chloridazon | 700 | 54 | — | 63 | — | 64 | — | 57 | — | 46 | — |
| Compound 36 + Chloridazon | 4 + 700 | 57 | 54 | 67 | 63 | 83 | 74 | 78 | 69 | 63 | 57 |
| Compound 36 + Chloridazon | 8 + 350 | 56 | 31 | 54 | 31 | 95 | 68 | 96 | 67 | 88 | 59 |
| Compound 36 + Chloridazon | 16 + 175 | 38 | 30 | 31 | 26 | 79 | 76 | 82 | 75 | 71 | 67 |

TABLE 27

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 27 | — | 28 | — | 20 | — |
| Compound 36 | 8 | 5 | — | 5 | — | 54 | — | 54 | — | 48 | — |
| Compound 36 | 16 | 20 | — | 14 | — | 72 | — | 72 | — | 64 | — |
| Bentazone | 125 | 0 | — | 0 | — | 9 | — | 10 | — | 8 | — |
| Bentazone | 250 | 0 | — | 0 | — | 22 | — | 22 | — | 18 | — |
| Bentazone | 500 | 0 | — | 0 | — | 49 | — | 52 | — | 45 | — |

TABLE 27-continued

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 + Bentazone | 4 + 500 | 6 | 0 | 7 | 0 | 66 | 63 | 68 | 65 | 64 | 56 |
| Compound 36 + Bentazone | 8 + 250 | 22 | 5 | 21 | 5 | 88 | 64 | 90 | 64 | 91 | 57 |
| Compound 36 + Bentazone | 16 + 125 | 23 | 20 | 17 | 14 | 84 | 74 | 82 | 75 | 74 | 67 |

TABLE 28

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 27 | — | 28 | — | 20 | — |
| Compound 36 | 8 | 5 | — | 5 | — | 54 | — | 54 | — | 48 | — |
| Compound 36 | 16 | 20 | — | 14 | — | 72 | — | 72 | — | 64 | — |
| Bromoxynil | 50 | 0 | — | 0 | — | 12 | — | 5 | — | 7 | — |
| Bromoxynil | 100 | 0 | — | 0 | — | 30 | — | 20 | — | 21 | — |
| Bromoxynil | 200 | 0 | — | 0 | — | 60 | — | 48 | — | 51 | — |
| Compound 36 + Bromoxynil | 4 + 200 | 4 | 0 | 9 | 0 | 81 | 71 | 71 | 63 | 67 | 61 |
| Compound 36 + Bromoxynil | 8 + 100 | 21 | 5 | 22 | 5 | 93 | 68 | 95 | 63 | 85 | 59 |
| Compound 36 + Bromoxynil | 16 + 50 | 25 | 20 | 22 | 14 | 81 | 75 | 79 | 73 | 76 | 67 |

TABLE 29

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Compound 36 | 4 | 0 | — | 0 | — | 27 | — | 28 | — | 20 | — |
| Compound 36 | 8 | 5 | — | 5 | — | 54 | — | 54 | — | 48 | — |
| Compound 36 | 16 | 20 | — | 14 | — | 72 | — | 72 | — | 64 | — |
| Propanil | 375 | 11 | — | 7 | — | 10 | — | 10 | — | 10 | — |
| Propanil | 750 | 21 | — | 22 | — | 23 | — | 27 | — | 24 | — |
| Propanil | 1500 | 46 | — | 45 | — | 56 | — | 56 | — | 58 | — |
| Compound 36 + Propanil | 4 + 1500 | 51 | 46 | 53 | 45 | 72 | 68 | 78 | 68 | 74 | 66 |
| Compound 36 + Propanil | 8 + 750 | 48 | 25 | 47 | 25 | 85 | 65 | 90 | 66 | 92 | 60 |
| Compound 36 + Propanil | 16 + 375 | 31 | 28 | 27 | 20 | 84 | 75 | 78 | 75 | 76 | 68 |

Comparative Examples

The procedures related to Tables 30 to 36 below were carried out in the same manner as those related to Tables 4, 5, 10, 12, 15, 17 and 27, except that Butafenacil was used instead of the uracil compound. The left column of two columns for each grass in the following tables indicates measured mortality values, and the right column indicates calculated mortality values.

Table 30 below is for comparison with Table 4 and shows that an 8:300 mixture of compound 36 and Glyphosate showed the highest effect.

TABLE 30

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Butafenacil | 4 | 0 | — | 0 | — | 2 | — | 23 | — | 15 | — |
| Butafenacil | 8 | 0 | — | 0 | — | 35 | — | 45 | — | 35 | — |
| Butafenacil | 16 | 5 | — | 5 | — | 51 | — | 67 | — | 54 | — |
| Glyphosate | 150 | 12 | — | 8 | — | 8 | — | 9 | — | 11 | — |
| Glyphosate | 300 | 23 | — | 18 | — | 27 | — | 22 | — | 30 | — |
| Glyphosate | 600 | 48 | — | 46 | — | 59 | — | 47 | — | 64 | — |
| Butafenacil + Glyphosate | 4 + 600 | 52 | 48 | 52 | 46 | 68 | 60 | 75 | 59 | 69 | 69 |
| Butafenacil + Glyphosate | 8 + 300 | 26 | 23 | 19 | 18 | 52 | 52 | 66 | 57 | 64 | 55 |
| Butafenacil + Glyphosate | 16 + 150 | 16 | 16 | 21 | 13 | 59 | 55 | 76 | 70 | 67 | 59 |

Table 31 below is for comparison with Table 5 and shows that an 8:150 mixture of compound 36 and Glufosinate showed the highest effect.

TABLE 31

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Butafenacil | 4 | 0 | — | 0 | — | 2 | — | 23 | — | 15 | — |
| Butafenacil | 8 | 0 | — | 0 | — | 35 | — | 45 | — | 35 | — |
| (Butafenacil | 16 | 5 | — | 5 | — | 51 | — | 67 | — | 54 | — |
| Glufosinate | 75 | 15 | — | 11 | — | 7 | — | 5 | — | 13 | — |
| Glufosinate | 150 | 29 | — | 27 | — | 25 | — | 18 | — | 25 | — |
| Glufosinate | 300 | 60 | — | 57 | — | 49 | — | 46 | — | 56 | — |
| Butafenacil + Glufosinate | 4 + 300 | 62 | 60 | 67 | 57 | 58 | 50 | 73 | 58 | 71 | 63 |
| Butafenacil + Glufosinate | 8 + 150 | 30 | 29 | 28 | 27 | 58 | 51 | 65 | 55 | 55 | 51 |
| Butafenacil + Glufosinate | 16 + 75 | 24 | 19 | 26 | 16 | 55 | 54 | 72 | 69 | 66 | 60 |

Table 32 below is for comparison with Table 10 and shows that a 20:100 mixture and 40:50 mixture of compound 36 and Metamifop showed high effects.

TABLE 32

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| | | \multicolumn{10}{c}{Data (measured value/calculated value)} | | | | | | | | | |
| Butafenacil | 20 | 12 | — | 12 | — | 55 | — | 51 | — | 42 | — |
| Butafenacil | 40 | 30 | — | 40 | — | 94 | — | 99 | — | 90 | — |
| Butafenacil | 80 | 53 | — | 70 | — | 100 | — | 100 | — | 100 | — |
| Metamifop | 25 | 11 | — | 11 | — | 0 | — | 0 | — | 0 | — |
| Metamifop | 50 | 26 | — | 23 | — | 0 | — | 0 | — | 0 | — |
| Metamifop | 100 | 57 | — | 48 | — | 0 | — | 0 | — | 0 | — |
| Butafenacil + Metamifop | 20 + 100 | 76 | 62 | 64 | 54 | 56 | 55 | 60 | 51 | 50 | 42 |

TABLE 32-continued

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Butafenacil + Metamifop | 40 + 50 | 53 | 47 | 63 | 53 | 100 | 94 | 100 | 99 | 91 | 90 |
| Butafenacil + Metamifop | 80 + 25 | 63 | 58 | 81 | 73 | 100 | 100 | 100 | 100 | 100 | 100 |

Table 33 below is for comparison with Table 12 and shows that a 20:100 mixture, 40:50 mixture and 80:25 mixture of compound 36 and Clethodim showed high effects.

TABLE 33

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Butafenacil | 20 | 12 | — | 12 | — | 55 | — | 51 | — | 42 | — |
| Butafenacil | 40 | 30 | — | 40 | — | 94 | — | 99 | — | 90 | — |
| Butafenacil | 80 | 53 | — | 70 | — | 100 | — | 100 | — | 100 | — |
| Clethodim | 25 | 11 | — | 6 | — | 0 | — | 0 | — | 0 | — |
| Clethodim | 50 | 31 | — | 19 | — | 0 | — | 0 | — | 0 | — |
| Clethodim | 100 | 65 | — | 45 | — | 0 | — | 0 | — | 0 | — |
| Butafenacil + Clethodim | 20 + 100 | 76 | 69 | 58 | 52 | 62 | 55 | 59 | 51 | 42 | 42 |
| Butafenacil + Clethodim | 40 + 50 | 52 | 51 | 57 | 51 | 100 | 94 | 100 | 99 | 93 | 90 |
| Butafenacil + Clethodim | 80 + 25 | 60 | 58 | 73 | 72 | 100 | 100 | 100 | 100 | 100 | 100 |

Table 34 below is for comparison with Table 15 and shows that an 8:2.5 mixture of compound 36 and Trifloxysulfuron showed the highest effect.

TABLE 34

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Butafenacil | 4 | 0 | — | 0 | — | 14 | — | 28 | — | 20 | — |
| Butafenacil | 8 | 0 | — | 0 | — | 35 | — | 49 | — | 57 | — |
| Butafenacil | 16 | 10 | — | 15 | — | 46 | — | 71 | — | 74 | — |
| Trifloxysulfuron | 1.25 | 8 | — | 8 | — | 12 | — | 9 | — | 13 | — |
| Trifloxysulfuron | 2.5 | 24 | — | 26 | — | 28 | — | 25 | — | 30 | — |
| Trifloxysulfuron | 5 | 56 | — | 51 | — | 61 | — | 58 | — | 62 | — |
| Butafenacil + Trifloxysulfuron | 4 + 5 | 59 | 56 | 52 | 51 | 76 | 67 | 76 | 70 | 70 | 70 |
| Butafenacil + Trifloxysulfuron | 8 + 2.5 | 30 | 24 | 34 | 26 | 56 | 53 | 65 | 62 | 77 | 70 |
| Butafenacil + Trifloxysulfuron | 16 + 1.25 | 22 | 17 | 30 | 22 | 58 | 52 | 82 | 74 | 78 | 77 |

Table 35 below is for comparison with Table 17 and shows that an 8:200 mixture and 16:100 mixture of compound 36 and 2,4-D showed the highest effect.

TABLE 35

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Butafenacil | 4 | 0 | — | 0 | — | 5 | — | 10 | — | 15 | — |
| Butafenacil | 8 | 0 | — | 5 | — | 20 | — | 30 | — | 35 | — |
| Butafenacil | 16 | 5 | — | 10 | — | 35 | — | 45 | — | 60 | — |
| 2,4-D | 100 | 0 | — | 0 | — | 7 | — | 7 | — | 10 | — |
| 2,4-D | 200 | 0 | — | 0 | — | 21 | — | 24 | — | 22 | — |
| 2,4-D | 400 | 0 | — | 0 | — | 47 | — | 51 | — | 50 | — |
| Butafenacil + 2,4-D | 4 + 400 | 0 | 0 | 0 | 0 | 59 | 50 | 72 | 56 | 61 | 58 |
| Butafenacil + 2,4-D | 8 + 200 | 5 | 0 | 5 | 5 | 48 | 36 | 66 | 46 | 68 | 49 |
| Butafenacil + 2,4-D | 16 + 100 | 10 | 5 | 15 | 10 | 55 | 40 | 61 | 49 | 74 | 64 |

Table 36 below is for comparison with Table 27 and shows that an 8:250 mixture and 16:125 mixture of compound 36 and Bentazone showed the highest effect.

TABLE 36

| Component | g/ha | Echinochloa crus | | Digitaria sanguinalis | | Abutilon theophrasti | | Aeschynomene indica | | Xanthium spinosum | |
|---|---|---|---|---|---|---|---|---|---|---|---|
| Butafenacil | 4 | 0 | — | 0 | — | 15 | — | 20 | — | 10 | — |
| Butafenacil | 8 | 0 | — | 0 | — | 45 | — | 40 | — | 25 | — |
| Butafenacil | 16 | 10 | — | 5 | — | 60 | — | 65 | — | 55 | — |
| Bentazone | 125 | 0 | — | 0 | — | 9 | — | 10 | — | 8 | — |
| Bentazone | 250 | 0 | — | 0 | — | 22 | — | 22 | — | 18 | — |
| Bentazone | 500 | 0 | — | 0 | — | 49 | — | 52 | — | 45 | — |
| Butafenacil + Bentazone | 4 + 500 | 4 | 0 | 4 | 0 | 70 | 57 | 71 | 62 | 55 | 51 |
| Butafenacil + Bentazone | 8 + 250 | 9 | 0 | 10 | 0 | 65 | 57 | 69 | 53 | 58 | 38 |
| Butafenacil + Bentazone | 16 + 125 | 29 | 10 | 9 | 5 | 75 | 64 | 76 | 69 | 70 | 58 |

As described above, the mixture of the conventional nonselective herbicide and the uracil compound showed a higher herbicidal activity than that of each compound and also showed a higher herbicidal activity than the mixture comprising Butafenacil in place of the uracil compound.

Example 2

Herbicidal Composition for Dry Field Farming

In the case of herbicidal compositions for dry field farming, weeds at the initial growth stage (5 cm or less) in wheat and corn fields were treated with various concentrations of herbicidal compositions containing the uracil compounds and herbicidally active compounds.

Experimental Examples

Tables 37 to 48 below show the plant mortalities (herbicidal activities) obtained when *Alopecurus aequalis, Porippa islandica, Capsella bursapastoris, Lamium amplexicaule* and wheat or *Echinochloa crus, Digitaria sanguinalis, Abutilon theophrasti, Aeschynomene indica* and corn were treated with the indicated amounts of uracil compounds, dry-field farming herbicides, and uracil compound/dry-field farming herbicide mixtures. When the measured values are higher than the calculated values, the test materials are regarded to have significant herbicidal activities. The left column of two columns for each grass in the following tables indicates measured mortality values, and the right column indicates calculated mortality values.

TABLE 37

| Component | g/ha | Alopecurus aequalis | | Porippa islandica | | Capsella bursa-pastoris | | Lamium amplexicaule | | Wheat | |
|---|---|---|---|---|---|---|---|---|---|---|---|
| Compound 36 | 1 | 0 | — | 10 | — | 5 | — | 10 | — | 0 | — |
| Compound 36 | 2 | 0 | — | 30 | — | 25 | — | 30 | — | 0 | — |

TABLE 37-continued

| Component | g/ha | Alopecurus aequalis | | Porippa islandica | | Capsella bursa-pastoris | | Lamium amplexicaule | | Wheat | |
|---|---|---|---|---|---|---|---|---|---|---|---|
| | | \multicolumn{10}{c|}{Data (measured value/calculated value)} |
| Compound 36 | 4 | 10 | — | 55 | — | 45 | — | 50 | — | 1 | — |
| Isoproturon | 150 | 15 | — | 10 | — | 11 | — | 12 | — | 0 | — |
| Isoproturon | 300 | 32 | — | 26 | — | 29 | — | 25 | — | 0 | — |
| Isoproturon | 600 | 64 | — | 53 | — | 63 | — | 49 | — | 1 | — |
| Compound 36 + Isoproturon | 1 + 600 | 74 | 64 | 62 | 58 | 69 | 65 | 59 | 54 | 1 | 1 |
| Compound 36 + Isoproturon | 2 + 300 | 56 | 32 | 76 | 48 | 75 | 46 | 77 | 47 | 0 | 0 |
| Compound 36 + Isoproturon | 4 + 150 | 29 | 24 | 68 | 59 | 56 | 51 | 60 | 56 | 1 | 1 |

TABLE 38

| Component | g/ha | Alopecurus aequalis | | Porippa islandica | | Capsella bursa-pastoris | | Lamium amplexicaule | | Wheat | |
|---|---|---|---|---|---|---|---|---|---|---|---|
| Compound 36 | 1 | 0 | — | 10 | — | 5 | — | 10 | — | 0 | — |
| Compound 36 | 2 | 0 | — | 30 | — | 25 | — | 30 | — | 0 | — |
| Compound 36 | 4 | 10 | — | 55 | — | 45 | — | 50 | — | 1 | — |
| Mesosulfuron | 2 | 15 | — | 12 | — | 10 | — | 13 | — | 0 | — |
| Mesosulfuron | 4 | 32 | — | 27 | — | 30 | — | 26 | — | 0 | — |
| Mesosulfuron | 8 | 64 | — | 61 | — | 59 | — | 55 | — | 1 | — |
| Compound 36 + Mesosulfuron | 1 + 8 | 68 | 64 | 70 | 65 | 67 | 61 | 70 | 60 | 1 | 1 |
| Compound 36 + Mesosulfuron | 2 + 4 | 55 | 32 | 80 | 49 | 78 | 47 | 78 | 48 | 0 | 0 |
| Compound 36 + Mesosulfuron | 4 + 2 | 32 | 24 | 64 | 61 | 60 | 50 | 64 | 56 | 1 | 1 |

TABLE 39

| Component | g/ha | Alopecurus aequalis | | Porippa islandica | | Capsella bursapastoris | | Lamium amplexicaule | | Wheat | |
|---|---|---|---|---|---|---|---|---|---|---|---|
| Compound 36 | 1 | 0 | — | 10 | — | 5 | — | 10 | — | 0 | — |
| Compound 36 | 2 | 0 | — | 30 | — | 25 | — | 30 | — | 0 | — |
| Compound 36 | 4 | 10 | — | 55 | — | 45 | — | 50 | — | 1 | — |
| Metsulfuron | 1 | 0 | — | 5 | — | 7 | — | 11 | — | 0 | — |
| Metsulfuron | 2 | 0 | — | 20 | — | 24 | — | 29 | — | 0 | — |
| Metsulfuron | 4 | 0 | — | 45 | — | 48 | — | 57 | — | 0 | — |
| Compound 36 + Metsulfuron | 1 + 4 | 8 | 0 | 61 | 51 | 60 | 51 | 70 | 61 | 0 | 0 |
| Compound 36 + Metsulfuron | 2 + 2 | 15 | 0 | 73 | 44 | 70 | 43 | 79 | 50 | 0 | 0 |

TABLE 39-continued

| Component | g/ha | \multicolumn{2}{c}{Alopecurus aequalis} | \multicolumn{2}{c}{Porippa islandica} | \multicolumn{2}{c}{Capsella bursapastoris} | \multicolumn{2}{c}{Lamium amplexicaule} | \multicolumn{2}{c}{Wheat} |
|---|---|---|---|---|---|---|---|---|---|---|---|
| Compound 36 + Metsulfuron | 4 + 1 | 17 | 10 | 66 | 57 | 57 | 49 | 60 | 56 | 1 | 1 |

TABLE 40

| Component | g/ha | Alopecurus aequalis | | Porippa islandica | | Capsella bursapastoris | | Lamium amplexicaule | | Wheat | |
|---|---|---|---|---|---|---|---|---|---|---|---|
| Compound 36 | 1 | 0 | — | 10 | — | 5 | — | 10 | — | 0 | — |
| Compound 36 | 2 | 0 | — | 30 | — | 25 | — | 30 | — | 0 | — |
| Compound 36 | 4 | 10 | — | 55 | — | 45 | — | 50 | — | 1 | — |
| Diflufenican | 37.5 | 0 | — | 5 | — | 6 | — | 10 | — | 0 | — |
| Diflufenican | 75 | 0 | — | 20 | — | 21 | — | 24 | — | 0 | — |
| Diflufenican | 150 | 0 | — | 40 | — | 45 | — | 47 | — | 1 | — |
| Compound 36 + Diflufenican | 1 + 150 | 4 | 0 | 51 | 46 | 54 | 48 | 62 | 52 | 1 | 1 |
| Compound 36 + Diflufenican | 2 + 75 | 15 | 0 | 70 | 44 | 66 | 40 | 77 | 46 | 0 | 0 |
| Compound 36 + Diflufenican | 4 + 37.5 | 16 | 10 | 65 | 57 | 55 | 48 | 62 | 55 | 1 | 1 |

TABLE 41

| Component | g/ha | Echinochloa crus | | Digitaria sanguinalis | | Abutilon theophrasti | | Aeschynomene indica | | Corn | |
|---|---|---|---|---|---|---|---|---|---|---|---|
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Nicosulfuron | 5 | 10 | — | 7 | — | 8 | — | 11 | — | 0 | — |
| Nicosulfuron | 10 | 24 | — | 24 | — | 26 | — | 30 | — | 0 | — |
| Nicosulfuron | 20 | 50 | — | 50 | — | 62 | — | 65 | — | 0 | — |
| Compound 36 + Nicosulfuron | 1 + 20 | 57 | 50 | 55 | 50 | 78 | 68 | 76 | 69 | 0 | 0 |
| Compound 36 + Nicosulfuron | 2 + 10 | 58 | 24 | 55 | 24 | 88 | 52 | 85 | 47 | 0 | 0 |
| Compound 36 + Nicosulfuron | 4 + 5 | 20 | 15 | 20 | 16 | 61 | 54 | 54 | 51 | 1 | 1 |

TABLE 42

| Component | g/ha | Echinochloa crus | | Digitaria sanguinalis | | Abutilon theophrasti | | Aeschynomene indica | | Corn | |
|---|---|---|---|---|---|---|---|---|---|---|---|
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Iodosulfuron | 1.25 | 7 | — | 12 | — | 13 | — | 12 | — | 0 | — |
| Iodosulfuron | 2.5 | 24 | — | 27 | — | 30 | — | 24 | — | 0 | — |
| Iodosulfuron | 5 | 58 | — | 56 | — | 61 | — | 47 | — | 1 | — |
| Compound 36 + Iodosulfuron | 1 + 5 | 62 | 58 | 65 | 56 | 73 | 67 | 56 | 52 | 1 | 1 |
| Compound 36 + Iodosulfuron | 2 + 2.5 | 63 | 24 | 65 | 27 | 84 | 54 | 70 | 43 | 0 | 0 |
| Compound 36 + Iodosulfuron | 4 + 1.25 | 16 | 12 | 23 | 20 | 63 | 56 | 59 | 51 | 1 | 1 |

TABLE 43

| Component | g/ha | Echinochloa crus | | Digitaria sanguinalis | | Abutilon theophrasti | | Aeschynomene indica | | Corn | |
|---|---|---|---|---|---|---|---|---|---|---|---|
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Florasulam | 1 | 0 | — | 0 | — | 12 | — | 8 | — | 0 | — |
| Florasulam | 2 | 0 | — | 0 | — | 23 | — | 18 | — | 0 | — |
| Florasulam | 4 | 0 | — | 0 | — | 54 | — | 46 | — | 0 | — |
| Compound 36 + Florasulam | 1 + 4 | 3 | 0 | 3 | 0 | 69 | 61 | 60 | 51 | 0 | 0 |
| Compound 36 + Florasulam | 2 + 2 | 15 | 0 | 15 | 0 | 79 | 50 | 64 | 39 | 0 | 0 |
| Compound 36 + Florasulam | 4 + 1 | 9 | 5 | 14 | 10 | 63 | 56 | 56 | 49 | 1 | 1 |

TABLE 44

| Component | g/ha | Echinochloa crus | | Digitaria sanguinalis | | Abutilon theophrasti | | Aeschynomene indica | | Corn | |
|---|---|---|---|---|---|---|---|---|---|---|---|
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Mesotrione | 15 | 0 | — | 0 | — | 15 | — | 11 | — | 0 | — |
| Mesotrione | 30 | 5 | — | 5 | — | 29 | — | 27 | — | 0 | — |
| Mesotrione | 60 | 15 | — | 10 | — | 58 | — | 54 | — | 1 | — |
| Compound 36 + Mesotrione | 1 + 60 | 24 | 15 | 15 | 10 | 70 | 64 | 69 | 59 | 1 | 1 |

TABLE 44-continued

|  |  | \multicolumn{10}{c|}{Data (measured value/calculated value)} |
| --- | --- | --- | --- | --- | --- | --- | --- | --- | --- | --- | --- |
| Component | g/ha | \multicolumn{2}{c|}{Echinochloa crus} | \multicolumn{2}{c|}{Digitaria sanguinalis} | \multicolumn{2}{c|}{Abutilon theophrasti} | \multicolumn{2}{c|}{Aeschynomene indica} | \multicolumn{2}{c|}{Corn} |
| Compound 36 + Mesotrione | 2 + 30 | 21 | 5 | 22 | 5 | 87 | 54 | 72 | 45 | 0 | 0 |
| Compound 36 + Mesotrione | 4 + 15 | 11 | 5 | 15 | 10 | 61 | 57 | 57 | 51 | 1 | 1 |

TABLE 45

| Component | g/ha | Echinochloa crus | | Digitaria sanguinalis | | Abutilon theophrasti | | Aeschynomene indica | | Corn | |
| --- | --- | --- | --- | --- | --- | --- | --- | --- | --- | --- | --- |
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Isoxaflutole | 12.5 | 14 | — | 10 | — | 12 | — | 9 | — | 0 | — |
| Isoxaflutole | 25 | 29 | — | 24 | — | 31 | — | 28 | — | 0 | — |
| Isoxaflutole | 50 | 61 | — | 53 | — | 62 | — | 56 | — | 0 | — |
| Compound 36 + Isoxaflutole | 1 + 50 | 67 | 61 | 60 | 53 | 75 | 68 | 69 | 60 | 0 | 0 |
| Compound 36 + Isoxaflutole | 2 + 25 | 65 | 29 | 58 | 24 | 89 | 55 | 85 | 46 | 0 | 0 |
| Compound 36 + Isoxaflutole | 4 + 12.5 | 25 | 19 | 28 | 19 | 65 | 56 | 58 | 50 | 1 | 1 |

TABLE 46

| Component | g/ha | Echinochloa crus | | Digitaria sanguinalis | | Abutilon theophrasti | | Aeschynomene indica | | Corn | |
| --- | --- | --- | --- | --- | --- | --- | --- | --- | --- | --- | --- |
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Flufenacet | 87.5 | 7 | — | 7 | — | 9 | — | 6 | — | 0 | — |
| Flufenacet | 175 | 24 | — | 22 | — | 23 | — | 18 | — | 0 | — |
| Flufenacet | 350 | 50 | — | 53 | — | 46 | — | 46 | — | 1 | — |
| Compound 36 + Flufenacet | 1 + 350 | 56 | 50 | 60 | 53 | 61 | 54 | 59 | 51 | 1 | 1 |
| Compound 36 + Flufenacet | 2 + 175 | 60 | 24 | 58 | 22 | 85 | 50 | 75 | 39 | 0 | 0 |
| Compound 36 + Flufenacet | 4 + 87.5 | 15 | 12 | 24 | 16 | 63 | 54 | 56 | 48 | 1 | 1 |

TABLE 47

| Component | g/ha | Echinochloa crus | | Digitaria sanguinalis | | Abutilon theophrasti | | Aeschynomene indica | | Corn | |
|---|---|---|---|---|---|---|---|---|---|---|---|
| | | \multicolumn{12}{c}{Data (measured value/calculated value)} |
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Sulfentrazone | 75 | 0 | — | 0 | — | 12 | — | 7 | — | 0 | — |
| Sulfentrazone | 150 | 5 | — | 10 | — | 25 | — | 25 | — | 0 | — |
| Sulfentrazone | 300 | 20 | — | 28 | — | 56 | — | 53 | — | 1 | — |
| Compound 36 + Sulfentrazone | 1 + 300 | 23 | 20 | 31 | 28 | 66 | 63 | 66 | 58 | 1 | 1 |
| Compound 36 + Sulfentrazone | 2 + 150 | 22 | 5 | 28 | 10 | 80 | 51 | 78 | 43 | 0 | 0 |
| Compound 36 + Sulfentrazone | 4 + 75 | 9 | 5 | 16 | 10 | 60 | 56 | 58 | 49 | 1 | 1 |

TABLE 48

| Component | g/ha | Echinochloa crus | | Digitaria sanguinalis | | Abutilon theophrasti | | Aeschynomene indica | | Corn | |
|---|---|---|---|---|---|---|---|---|---|---|---|
| | | \multicolumn{12}{c}{Data (measured value/calculated value)} |
| Compound 36 | 1 | 0 | — | 0 | — | 15 | — | 10 | — | 0 | — |
| Compound 36 | 2 | 0 | — | 0 | — | 35 | — | 25 | — | 0 | — |
| Compound 36 | 4 | 5 | — | 10 | — | 50 | — | 45 | — | 1 | — |
| Carfentrazone | 2.5 | 0 | — | 0 | — | 30 | — | 20 | — | 0 | — |
| Carfentrazone | 5 | 0 | — | 0 | — | 50 | — | 45 | — | 0 | — |
| Carfentrazone | 10 | 5 | — | 5 | — | 75 | — | 70 | — | 1 | — |
| Compound 36 + Carfentrazone | 1 + 10 | 13 | 5 | 9 | 5 | 85 | 79 | 77 | 73 | 1 | 1 |
| Compound 36 + Carfentrazone | 2 + 5 | 15 | 0 | 15 | 0 | 90 | 68 | 92 | 59 | 0 | 0 |
| Compound 36 + Carfentrazone | 4 + 2.5 | 14 | 5 | 16 | 10 | 75 | 65 | 63 | 56 | 1 | 1 |

Comparative Examples

The procedures related to Tables 49 and 50 below were carried out in the same manner as the procedures related to Tables 38 and 44, except that Carfentrazone was used in place of the uracil compound. The left column of two columns for each grass in the following tables indicates measured mortality values, and the right column indicates calculated mortality values.

Table 49 below is for comparison with Table 38 and shows that a 2:4 mixture of compound 36 and Carfentrazone showed the highest herbicidal effect.

TABLE 49

| Component | g/ha | Alopecurus aequalis | | Porippa islandica | | Capsella bursapastoris | | Lamium amplexicaule | | Wheat | |
|---|---|---|---|---|---|---|---|---|---|---|---|
| | | \multicolumn{12}{c}{Data (measured value/calculated value)} |
| Carfentrazone | 1 | 0 | — | 5 | — | 0 | — | 5 | — | 0 | — |
| Carfentrazone | 2 | 0 | — | 15 | — | 15 | — | 20 | — | 0 | — |
| Carfentrazone | 4 | 0 | — | 40 | — | 35 | — | 40 | — | 0 | — |
| Mesosulfuron | 2 | 15 | — | 12 | — | 10 | — | 13 | — | 0 | — |
| Mesosulfuron | 4 | 32 | — | 27 | — | 30 | — | 26 | — | 0 | — |
| Mesosulfuron | 8 | 64 | — | 61 | — | 59 | — | 55 | — | 1 | — |
| Carfentrazone + Mesosulfuron | 1 + 8 | 68 | 64 | 63 | 63 | 65 | 59 | 68 | 57 | 1 | 1 |

TABLE 49-continued

| Component | g/ha | Alopecurus aequalis | | Porippa islandica | | Capsella bursapastoris | | Lamium amplexicaule | | Wheat | |
|---|---|---|---|---|---|---|---|---|---|---|---|
| | | \multicolumn{10}{c}{Data (measured value/calculated value)} | | | | | | | | | |
| Carfentrazone + Mesosulfuron | 2 + 4 | 33 | 32 | 37 | 38 | 52 | 40 | 55 | 40 | 1 | 0 |
| Carfentrazone + Mesosulfuron | 4 + 2 | 23 | 15 | 15 | 47 | 50 | 41 | 60 | 48 | 0 | 0 |

Table 50 below is for comparison with Table 44 and shows that a 2:30 mixture and 4:15 mixture of compound 36 and Mesotrione showed the highest herbicidal effect.

TABLE 50

| Component | g/ha | Echinochloa crus | | Digitaria sanguinalis | | Abutilon theophrasti | | Aeschynomene indica | | Corn | |
|---|---|---|---|---|---|---|---|---|---|---|---|
| | | \multicolumn{10}{c}{Data (measured value/calculated value)} | | | | | | | | | |
| Carfentrazone | 1 | 0 | — | 0 | — | 10 | — | 5 | — | 0 | — |
| Carfentrazone | 2 | 0 | — | 0 | — | 25 | — | 20 | — | 0 | — |
| Carfentrazone | 4 | 0 | — | 0 | — | 45 | — | 40 | — | 0 | — |
| Mesotrione | 15 | 0 | — | 0 | — | 15 | — | 11 | — | 0 | — |
| Mesotrione | 30 | 5 | — | 5 | — | 29 | — | 27 | — | 0 | — |
| Mesotrione | 60 | 15 | — | 10 | — | 58 | — | 54 | — | 1 | — |
| Carfentrazone + Mesotrione | 1 + 60 | 20 | 15 | 20 | 10 | 70 | 62 | 68 | 56 | 1 | 1 |
| Carfentrazone + Mesotrione | 2 + 30 | 14 | 5 | 7 | 5 | 60 | 47 | 55 | 42 | 0 | 0 |
| Carfentrazone + Mesotrione | 4 + 15 | 8 | 0 | 4 | 0 | 65 | 53 | 60 | 46 | 1 | 0 |

As can be seen in Tables 37 to 50 above, the mixture of the uracil compound and the conventional dry-field farming herbicide showed a higher herbicidal activity than that of each compound and also showed a higher herbicidal activity of the mixture comprising Carfentrazone in place of the uracil compound. In addition, the mixture of the uracil compound and the conventional dry-field farming herbicide did not show herbicidal activity for wheat and corn, suggesting that it can be used as a herbicidal composition for dry-field farming.

Example 3

Herbicidal Composition for Paddy Field Farming

In the case of herbicidal compositions, weeds in rice fields were treated with compositions comprising the above uracil composition and herbicidally active compound at 25 days after rice transplantation.

Experimental Examples

Tables 51 and 52 below show the plant mortalities (herbicidal activities) obtained when *Monochoria vaginalis*, *Ludwigia prostrate* and a rice plant were treated with the indicated amounts of uracil compounds, paddy field farming herbicides, and uracil compound/paddy field farming herbicide mixtures, and Tables 53 to 77 below show the plant mortalities obtained when *Monochoria vaginalis* and *Echinochloa crus* were treated with the indicated amounts. When the measured values are higher than the calculated values, the test materials are regarded to have significant herbicidal activities. The left column of two columns for each grass in the following tables indicates measured mortality values, and the right column indicates calculated mortality values.

TABLE 51

| Component | g/ha | Monochoria vaginalis | | Ludwigia prostrate | | Rice plant | |
|---|---|---|---|---|---|---|---|
| | | \multicolumn{6}{c}{Data (measured value/calculated value)} | | | | | |
| Compound 36 | 2.5 | 5 | — | 15 | — | 0 | — |
| Compound 36 | 5 | 30 | — | 35 | — | 0 | — |
| Compound 36 | 10 | 50 | — | 55 | — | 1 | — |
| Bensulfuron | 10 | 15 | — | 20 | — | 0 | — |
| Compound Bensulfuron | 20 | 35 | — | 40 | — | 0 | — |
| Bensulfuron | 40 | 51 | — | 55 | — | 1 | — |

TABLE 51-continued

| Component | g/ha | Monochoria vaginalis | | Ludwigia prostrate | | Rice plant | |
|---|---|---|---|---|---|---|---|
| | | \multicolumn{2}{c}{Data (measured value/calculated value)} | | | | |
| Compound 36 + Bensulfuron | 2.5 + 40 | 56 | 53 | 66 | 62 | 1 | 1 |
| Compound 36 + Bensulfuron | 5 + 20 | 88 | 55 | 96 | 61 | 0 | 0 |
| Compound 36 + Bensulfuron | 10 + 10 | 62 | 58 | 68 | 64 | 1 | 1 |

TABLE 52

| Component | g/ha | Monochoria vaginalis | | Ludwigia prostrate | | Rice plant | |
|---|---|---|---|---|---|---|---|
| Compound 36 | 2.5 | 5 | — | 15 | — | 0 | — |
| Compound 36 | 5 | 30 | — | 35 | — | 0 | — |
| Compound 36 | 10 | 50 | — | 55 | — | 1 | — |
| Pyrazosulfuron | 2.5 | 15 | — | 20 | — | 0 | — |
| Pyrazosulfuron | 5 | 40 | — | 45 | — | 0 | — |
| Pyrazosulfuron | 10 | 67 | — | 62 | — | 1 | — |
| Compound 36 + Pyrazosulfuron | 2.5 + 10 | 79 | 69 | 71 | 68 | 1 | 1 |
| Compound 36 + Pyrazosulfuron | 5 + 5 | 88 | 58 | 100 | 64 | 0 | 0 |
| Compound 36 + Pyrazosulfuron | 10 + 2.5 | 61 | 58 | 67 | 64 | 1 | 1 |

TABLE 53

| Component | g/ha | Monochoria vaginalis | | Echinochloa crus | |
|---|---|---|---|---|---|
| Compound 36 | 5 | 30 | — | 0 | — |
| Azimsulfuron | 5 | 50 | — | 30 | — |
| Compound 36 + Azimsulfuron | 5 + 5 | 90 | 65 | 55 | 30 |

TABLE 54

| Component | g/ha | Monochoria vaginalis | | Echinochloa crus | |
|---|---|---|---|---|---|
| Compound 36 | 5 | 30 | — | 0 | — |
| Cinosulfuron | 10 | 30 | — | 20 | — |
| Compound 36 + Cinosulfuron | 5 + 10 | 80 | 51 | 45 | 20 |

TABLE 55

| Component | g/ha | Monochoria vaginalis | | Echinochloa crus | |
|---|---|---|---|---|---|
| Compound 36 | 5 | 30 | — | 0 | — |
| Cyclosulfamuron | 11 | 50 | — | 30 | — |
| Compound 36 + Cyclosulfamuron | 5 + 11 | 90 | 65 | 45 | 30 |

TABLE 56

| Component | g/ha | Monochoria vaginalis | | Echinochloa crus | |
|---|---|---|---|---|---|
| Compound 36 | 5 | 30 | — | 0 | — |
| Halosulfuron | 11 | 30 | — | 30 | — |
| Compound 36 + Halosulfuron | 5 + 11 | 85 | 51 | 40 | 20 |

TABLE 57

| Component | g/ha | Monochoria vaginalis | | Echinochloa crus | |
|---|---|---|---|---|---|
| Compound 36 | 5 | 30 | — | 0 | — |
| Imazosulfuron | 18 | 40 | — | 20 | — |
| Compound 36 + Imazosulfuron | 5 + 18 | 90 | 58 | 45 | 20 |

TABLE 58

| Component | g/ha | Monochoria vaginalis | | Echinochloa crus | |
|---|---|---|---|---|---|
| Compound 36 | 5 | 30 | — | 0 | — |
| Orthosulfamuron | 17.5 | 40 | — | 10 | — |
| Compound 36 + Orthosulfamuron | 5 + 17.5 | 85 | 58 | 35 | 10 |

TABLE 59

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Pyriminobac | 11 | 0 | — | 50 | — |
| Compound 36 + Pyriminobac | 5 + 11 | 55 | 30 | 85 | 50 |

TABLE 60

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Pyrimisulfan | 16.5 | 50 | — | 40 | — |
| Compound 36 + Pyrimisulfan | 5 + 16.5 | 95 | 65 | 65 | 40 |

TABLE 61

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Propyrisulfuron | 18 | 45 | — | 45 | — |
| Compound 36 + Propyrisulfuron | 5 + 18 | 90 | 61.5 | 70 | 45 |

TABLE 62

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Metazosulfuron | 25 | 40 | — | 35 | — |
| Compound 36 + Metazosulfuron | 5 + 25 | 90 | 58 | 65 | 35 |

TABLE 63

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Triafamone | 12.5 | 10 | — | 50 | — |
| Compound 36 + Triafamone | 5 + 12.5 | 70 | 37 | 80 | 50 |

TABLE 64

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Anilofos | 75 | 0 | — | 50 | — |
| Compound 36 + Anilofos | 5 + 75 | 55 | 30 | 85 | 50 |

TABLE 65

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Benzobicyclon | 50 | 30 | — | 0 | — |
| Compound 36 + Benzobicyclon | 5 + 50 | 80 | 51 | 30 | 0 |

TABLE 66

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Bromobutide | 225 | 50 | — | 0 | — |
| Compound 36 + Bromobutide | 5 + 225 | 90 | 65 | 20 | 0 |

TABLE 67

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Cafenstrole | 50 | 30 | — | 20 | — |
| Compound 36 + Cafenstrole | 5 + 50 | 85 | 51 | 45 | 20 |

TABLE 68

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Esprocarb | 500 | 30 | — | 20 | — |
| Compound 36 + Esprocarb | 5 + 500 | 85 | 51 | 55 | 20 |

TABLE 69

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Ethoxysulfuron | 15 | 20 | — | 10 | — |
| Compound 36 + Ethoxysulfuron | 5 + 15 | 80 | 44 | 35 | 10 |

TABLE 70

| Component | g/ha | Data (measured value/calculated value) | | | |
|---|---|---|---|---|---|
| | | *Monochoria vaginalis* | | *Echinochloa crus* | |
| Compound 36 | 5 | 30 | — | 0 | — |
| Fentrazamide | 50 | 30 | — | 20 | — |
| Compound 36 + Fentrazamide | 5 + 50 | 85 | 51 | 45 | 20 |

TABLE 71

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| Indanofan | 37.5 | 0 | — | 25 | — |
| Compound 36 + Indanofan | 5 + 37.5 | 65 | 30 | 50 | 25 |

TABLE 72

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| Mefenacet | 200 | 30 | — | 30 | — |
| Compound 36 + Mefenacet | 5 + 200 | 80 | 51 | 55 | 30 |

TABLE 73

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| molinate | 500 | 0 | — | 50 | — |
| Compound 36 + molinate | 5 + 500 | 50 | 30 | 80 | 50 |

TABLE 74

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| Oxaziclomefone | 12.5 | 0 | — | 30 | — |
| Compound 36 + Oxaziclomefone | 5 + 12.5 | 55 | 30 | 65 | 30 |

TABLE 75

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| Pyributicarb | 150 | 20 | — | 20 | — |
| Compound 36 + Pyributicarb | 5 + 150 | 75 | 44 | 45 | 20 |

TABLE 76

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| Pyritlalid | 37.5 | 0 | — | 30 | — |
| Compound 36 + Pyritlalid | 5 + 37.5 | 65 | 30 | 50 | 30 |

TABLE 77

| Component | g/ha | Data (measured value/calculated value) | | | |
|---|---|---|---|---|---|
| | | Monochoria vaginalis | | Echinochloa crus | |
| Compound 36 | 5 | 30 | — | 0 | — |
| Quinoclamine | 450 | 0 | — | 0 | — |
| Compound 36 + Quinoclamine | 5 + 450 | 65 | 30 | 25 | 0 |

Comparative Example

The procedure related to Table 78 below was carried out in the same manner as the procedure related to Table 52, except that Carfentrazone was used in place of the uracil compound.

Table 78 below is for comparison with Table 52 and shows that a 2.5:10 mixture and 5:5 mixture of compound 36 and Pyrazosulfuron showed the highest herbicidal effect. The left column of two columns for each grass in the following table indicates measured mortality values, and the right column indicates calculated mortality values.

TABLE 78

| Component | g/ha | Data (measured value/calculated value) | | | | | |
|---|---|---|---|---|---|---|---|
| | | Monochoria vaginalis | | Ludwigia prostrate | | Rice plant | |
| Carfentrazone | 2.5 | 0 | — | 10 | — | 0 | — |
| Carfentrazone | 5 | 20 | — | 35 | — | 0 | — |
| Carfentrazone | 10 | 45 | — | 50 | — | 0 | — |
| Pyrazosulfuron | 2 | 20 | — | 15 | — | 0 | — |
| Pyrazosulfuron | 4 | 40 | — | 35 | — | 0 | — |
| Pyrazosulfuron | 8 | 63 | — | 65 | — | 1 | — |
| Carfentrazone + Pyrazosulfuron | 2.5 + 8 | 70 | 63 | 72 | 69 | 1 | 1 |
| Carfentrazone + Pyrazosulfuron | 5 + 4 | 60 | 52 | 60 | 58 | 1 | 0 |
| Carfentrazone + Pyrazosulfiwon | 10 + 2 | 65 | 56 | 65 | 58 | 0 | 0 |

As can be seen in Tables 51 to 78 above, the mixture of the uracil compound and the conventional paddy field farming herbicide showed a higher herbicidal activity than that of each compound and also showed a higher herbicidal activity of the mixture comprising Carfentrazone in place of the uracil compound. In addition, the mixture of the uracil compound and the conventional paddy field farming herbicide did not show herbicidal activity for the rice plant, suggesting that it can be used as an herbicidal composition for paddy field farming.

Example 4

Nonselective Herbicidal Composition Comprising 1 Uracil Compound and 2 Herbicidally Active Compounds Weeds at the weed growth stage (30-40 cm) in fallow areas and orchards were treated with nonselective herbicidal compositions containing 1 uracil compound and 2 herbicidally active compounds.

Experimental Example

Tables 79 below show the plant mortalities (herbicidal activities) obtained when ryegrass and wild amaranth were treated with the indicated amounts of nonselective herbicides, and 1 uracil compound/2 herbicide mixtures. When the measured values are higher than the calculated values, the test materials have significant herbicidal activities. The left column of two columns for each grass in the following tables indicates measured mortality values, and the right column indicates calculated mortality values.

TABLE 79

| component | g ai/ha | ryegrass | | Wild amaranth | |
|---|---|---|---|---|---|
| | | \multicolumn{4}{c}{Data (measured value/calculated value)} | | | |
| compound 36 | 8 | 30 | — | 40 | — |
| Glyphosate-IPA | 300 | 10 | — | 10 | — |
| compound 36 + Glyphosate-IPA | 8 + 300 | 65 | 37 | 80 | 46 |
| Clopyralid | 125 | 0 | — | 10 | — |
| compound 36 + Glyphosate-IPA + Clopyralid | 8 + 300 + 125 | 95 | 65 | 100 | 82 |
| compound 36 + Glyphosate-IPA | 8 + 300 | 65 | 37 | 80 | 46 |
| Sulcotrione | 75 | 20 | — | 20 | — |
| compound 36 + Glyphosate-IPA + Sulcotrione | 8 + 300 + 75 | 98 | 72 | 100 | 84 |
| compound 36 + Glyphosate-IPA | 8 + 300 | 65 | 37 | 80 | 46 |
| Clomazone | 175 | 15 | — | 30 | — |
| compound 36 + Glyphosate-IPA + Clomazone | 8 + 300 + 175 | 99 | 70 | 100 | 86 |
| compound 36 + Glyphosate-IPA | 8 + 300 | 65 | 37 | 80 | 46 |
| Picolinafen | 25 | 0 | — | 25 | — |
| compound 36 + Glyphosate-IPA + Picolinafen | 8 + 300 + 25 | 85 | 65 | 100 | 85 |
| compound 36 + Glyphosate-IPA | 8 + 300 | 65 | 37 | 80 | 46 |
| Imazamox | 8.3 | 30 | — | 20 | — |
| compound 36 + Glyphosate-IPA + Imazamox | 8 + 300 + 8.3 | 100 | 76 | 99 | 84 |
| compound 36 + Glyphosate-IPA | 8 + 300 | 65 | 37 | 80 | 46 |
| Diclofop | 175 | 30 | — | 0 | — |
| compound 36 + Glyphosate-IPA + Diclofop | 8 + 300 + 175 | 99 | 76 | 90 | 80 |
| compound 36 + Glyphosate-IPA | 8 + 300 | 65 | 37 | 80 | 46 |
| Diflufenzopyr | 12.5 | 20 | — | 20 | — |
| compound 36 + Glyphosate-IPA + Diflufenzopyr | 8 + 300 + 12.5 | 93 | 72 | 99 | 84 |
| compound 36 + Glyphosate-IPA | 8 + 300 | 65 | 37 | 80 | 46 |
| Isoxaben | 31 | 0 | — | 30 | — |
| compound 36 + Glyphosate-IPA + Isoxaben | 8 + 300 +31 | 85 | 65 | 100 | 86 |
| compound 36 + Glyphosate-IPA | 8 + 300 | 65 | 37 | 80 | 46 |
| Asulam | 1250 | 25 | — | 20 | — |
| compound 36 + Glyphosate-IPA + Asulam | 8 + 300 + 1250 | 98 | 74 | 99 | 84 |
| compound 36 + Glyphosate-IPA | 8 + 300 | 65 | 37 | 80 | 46 |
| Bilanafos | 500 | 30 | — | 15 | — |
| compound 36 + Glyphosate-IPA + Bilanafos | 8 + 300 + 500 | 100 | 76 | 99 | 83 |
| compound 36 + Glyphosate-IPA | 8 + 300 | 65 | 37 | 80 | 46 |
| Ethofumesate | 250 | 25 | — | 20 | — |
| compound 36 + Glyphosate-IPA + Ethofumesate | 8 + 300 + 250 | 99 | 74 | 95 | 84 |
| compound 36 + Glyphosate-IPA | 8 + 300 | 65 | 37 | 80 | 46 |
| Atrazine | 200 | 30 | — | 25 | — |
| compound 36 + Glyphosate-IPA + Atrazine | 8 + 300 + 200 | 100 | 76 | 100 | 85 |
| compound 36 + Glyphosate-IPA | 8 + 300 | 65 | 37 | 80 | 46 |
| Oxadiazon | 500 | 30 | — | 30 | — |
| compound 36 + Glyphosate-IPA + Oxadiazon | 8 + 300 +5 00 | 100 | 76 | 100 | 86 |
| compound 36 + Glyphosate-IPA | 8 + 300 | 65 | 37 | 80 | 46 |
| Acetochlor | 375 | 30 | — | 10 | — |
| compound 36 + Glyphosate-IPA + Acetochlor | 8 + 300 + 375 | 100 | 76 | 95 | 82 |

TABLE 79-continued

|  | | Data (measured value/calculated value) | | | |
| --- | --- | --- | --- | --- | --- |
| component | g ai/ha | ryegrass | | Wild amaranth | |
| compound 36 + Glyphosate-IPA | 8 + 300 | 65 | 37 | 80 | 46 |
| Pendimethalin | 250 | 30 | — | 20 | — |
| compound 36 + Glyphosate-IPA + Pendimethalin | 8 + 300 + 250 | 100 | 76 | 98 | 84 |
| compound 36 + Glyphosate-IPA | 8 + 300 | 65 | 37 | 80 | 46 |
| Aminopyralid | 250 | 0 | — | 20 | — |
| compound 36 + Glyphosate-IPA + Aminopyralid | 8 + 300 +250 | 80 | 65 | 100 | 84 |
| compound 36 | 8 | 30 | — | 40 | — |
| Glufosinate-ammonium | 150 | 10 | — | 20 | — |
| compound 36 + Glufosinate-ammonium | 8 + 150 | 60 | 37 | 85 | 52 |
| Clopyralid | 125 | 0 | — | 10 | — |
| compound 36 + Glufosinate-ammonium + Clopyralid | 8 + 150 + 125 | 90 | 60 | 100 | 87 |
| compound 36 + Glufosinate-ammonium | 8 + 300 | 65 | 37 | 80 | 46 |
| Sulcotrione | 75 | 20 | — | 20 | — |
| compound 36 + Glufosinate-ammonium + Sulcotrione | 8 + 300 + 75 | 95 | 72 | 98 | 84 |
| compound 36 + Glufosinate-ammonium | 8 + 300 | 65 | 37 | 80 | 46 |
| Clomazone | 175 | 15 | — | 30 | — |
| compound 36 + Glufosinate-ammonium + Clomazone | 8 + 300 + 175 | 95 | 70 | 99 | 86 |
| compound 36 + Glufosinate-ammonium | 8 + 300 | 65 | 37 | 80 | 46 |
| Picolinafen | 25 | 0 | — | 25 | — |
| compound 36 + Glufosinate-ammonium + Picolinafen | 8 + 300 + 25 | 85 | 65 | 99 | 85 |
| compound 36 + Glufosinate-ammonium | 8 + 300 | 65 | 37 | 80 | 46 |
| Imazamox | 8.3 | 30 | — | 20 | — |
| compound 36 + Glufosinate-ammonium + Imazamox | 8 + 300 + 8.3 | 95 | 76 | 98 | 84 |
| compound 36 + Glufosinate-ammonium | 8 + 300 | 65 | 37 | 80 | 46 |
| Diclofop | 175 | 30 | — | 0 | — |
| compound 36 + Glufosinate-ammonium + Diclofop | 8 + 300 + 175 | 99 | 76 | 90 | 80 |
| compound 36 + Glufosinate-ammonium | 8 + 300 | 65 | 37 | 80 | 46 |
| Diflufenzopyr | 12.5 | 20 | — | 20 | — |
| compound 36 + Glufosinate-ammonium + Diflufenzopyr | 8 + 300 + 12.5 | 95 | 72 | 95 | 84 |
| compound 36 + Glufosinate-ammonium | 8 + 300 | 65 | 37 | 80 | 46 |
| Isoxaben | 31 | 0 | — | 30 | — |
| compound 36 + Glufosinate-ammonium + Isoxaben | 8 + 300 +31 | 80 | 65 | 100 | 86 |
| compound 36 + Glufosinate-ammonium | 8 + 300 | 65 | 37 | 80 | 46 |
| Asulam | 1250 | 25 | — | 20 | — |
| compound 36 + Glufosinate-ammonium + Asulam | 8 + 300 + 1250 | 95 | 74 | 98 | 84 |
| compound 36 + Glufosinate-ammonium | 8 + 300 | 65 | 37 | 80 | 46 |
| Bilanafos | 500 | 30 | — | 15 | — |
| compound 36 + Glufosinate-ammonium + Bilanafos | 8 + 300 + 500 | 98 | 76 | 95 | 83 |
| compound 36 + Glufosinate-ammonium | 8 + 300 | 65 | 37 | 80 | 46 |
| Ethofiimesate | 250 | 25 | — | 20 | — |
| compound 36 + Glufosinate-ammonium + Ethofiimesate | 8 + 300 + 250 | 98 | 74 | 93 | 84 |
| compound 36 + Glufosinate-ammonium | 8 + 300 | 65 | 37 | 80 | 46 |
| Atrazine | 200 | 30 | — | 25 | — |
| compound 36 + Glufosinate-ammonium + Atrazine | 8 + 300 + 200 | 98 | 76 | 99 | 85 |
| compound 36 + Glufosinate-ammonium | 8 + 300 | 65 | 37 | 80 | 46 |

TABLE 79-continued

| component | g ai/ha | Data (measured value/calculated value) | | | |
|---|---|---|---|---|---|
| | | ryegrass | | Wild amaranth | |
| Oxadiazon | 500 | 30 | — | 30 | — |
| compound 36 + Glufosinate-ammonium + Oxadiazon | 8 + 300 + 500 | 99 | 76 | 100 | 86 |
| compound 36 + Glufosinate-ammonium | 8 + 300 | 65 | 37 | 80 | 46 |
| Acetochlor | 375 | 30 | — | 10 | — |
| compound 36 + Glufosinate-ammonium + Acetochlor | 8 + 300 + 375 | 100 | 76 | 93 | 82 |
| compound 36 + Glufosinate-ammonium | 8 + 300 | 65 | 37 | 80 | 46 |
| Pendimethalin | 250 | 30 | — | 20 | — |
| compound 36 + Glufosinate-ammonium + Pendimethalin | 8 + 300 + 250 | 96 | 76 | 100 | 84 |
| compound 36 + Glufosinate-ammonium | 8 + 300 | 65 | 37 | 80 | 46 |
| Aminopyralid | 250 | 0 | — | 20 | — |
| compound 36 + Glufosinate-ammonium + Aminopyralid | 8 + 300 + 250 | 80 | 65 | 98 | 84 |

As described above, the mixture of the two conventional nonselective herbicide and the uracil compound showed a higher herbicidal activity.

As described above, the herbicidal composition according to the present invention comprises, as active ingredients, the uracil compound represented by formula 1 and an herbicidally active compound, and thus exhibits excellent herbicidal activity while having a very high compatibility with crops. In addition, the herbicidal composition of the present invention shows excellent effects not only on selective control of monocotyledonous and dicotyledonous weeds in various crops, for example, wheat, barley, oat and corn, but also on control of monocotyledonous and dicotyledonous weeds in semi- and non-selective areas.

As can be seen from the results of the above examples carried out by the present inventors, the inventive herbicidal composition comprising both the uracil compound and the herbicidally active compound showed excellent herbicidal activity thanks to the synergistic action of these active ingredients compared to the herbicidal composition comprising the uracil compound or the herbicidally active compound individually. This increased herbicidal activity is a remarkable effect which could not be predicted by those skilled in the art.

In addition, the herbicidal composition of the present invention could be tolerated by a variety of crops and could effectively control even weeds which are usually difficult to control. Thus, the herbicidal composition of the present invention is a broad-spectrum herbicidal composition.

Accordingly, the herbicidal composition of the present invention has excellent herbicidal activity against weeds, can selectively control monocotyledonous and dicotyledonous weeds in useful crops and can also control monocotyledonous and dicotyledonous weeds in semi-selective and non-selective areas.

What is claimed is:

1. An herbicidal composition comprising, as active ingredients, an herbicidally active compound and a uracil compound represented by the following formula 1 or an agrochemically acceptable salt thereof:

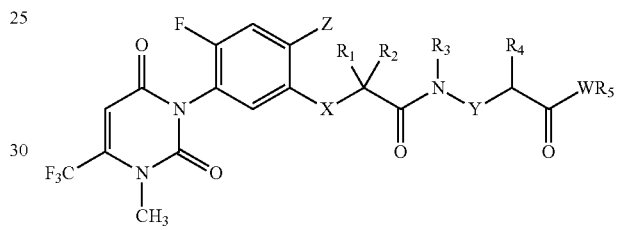

Formula 1 wherein R1 and R5 represent a methyl group;
R2, R3, and R4 represent a hydrogen atom;
X represents O, or S;
Y represents a methylene group;
W represents O; and
Z represents a chlorine atom,
wherein:
(a) if X represents O,
(1) the herbicidally active compound is glyphosate or glufosinate,
(2) a content ratio of the glyphosate to the uracil compound is 150:16 (9.375:1) to 600:4 (150:1), and
(3) a content ratio of the glufosinate to the uracil compound is 75:16 (4.6875:1) to 300:4 (75:1), and
(b) if X represents S,
(1) the herbicidally active compound is at least one selected from the group consisting of glyphosate, glufosinate, fenoxaprop, clodinafop, fluazifop, haloxyfop, metamifop, pinoxaden, clethodim, tralkoxydim, imazethapyr, trifloxysulfuron, bispyribac-sodium, 2,4-D, dicamba, picloram, fluroxypyr, triclopyr, MCPA, mecoprop, quinclorac, MCPB, chloridazon, bentazone, bromoxynil, propanil, mesosulfuron, metsulfuron, diflufenican, nicosulfuron, iodosulfuron, florasulam, mesotrione, isoxaflutole, flufenacet, sulfentrazone, carfentrazone, bensulfuron, and pyrazosulfuron,
(2) a content ratio of the glyphosate to the uracil compound is 150:16 (9.375:1) to 600:4 (150:1),
(3) a content ratio of the glufosinate to the uracil compound is 75:16 (4.6875:1) to 300:4 (75:1),
(4) a content ratio of the fenoxaprop to the uracil compound is 25:80 (0.3125:1) to 100:20 (5:1), (5) a content ratio of the clodinafop to the uracil compound is 7.5:80 (0.09375:1) to 30:20 (1.5:1),
(6) a content ratio of the fluazifop to the uracil compound is 50:80 (0.625:1) to 200:20 (10:1),
(7) a content ratio of the haloxyfop to the uracil compound is 12.5:80 (0.15625:1) to 50:20 (2.5:1),
(8) a content ratio of the metamifop to the uracil compound is 25:80 (0.3125:1) to 100:20 (5:1),
(9) a content ratio of the pinoxaden to the uracil compound is 6.25:80 (0.078125:1) to 25:20 (1.25:1),
(10) a content ratio of the clethodim to the uracil compound is 25:80 (0.3125:1) to 100:20 (5:1),
(11) a content ratio of the tralkoxydim to the uracil compound is 25:80 (0.3125:1) to 100:20 (5:1),
(12) a content ratio of the imazethapyr to the uracil compound is 25:16 (1.5625:1) to 100:4 (25:1),
(13) a content ratio of the trifloxysulfuron to the uracil compound is 1.25:16 (0.078125:1) to 5:4 (1.25:1),
(14) a content ratio of the bispyribac-sodium to the uracil compound is 7.5:16 (0.46875:1) to 30:4 (7.5:1),
(15) a content ratio of the 2,4-D to the uracil compound is 100:16 (6.25:1) to 400:4 (100:1),
(16) a content ratio of the dicamba to the uracil compound is 75:16 (4.6875:1) to 300:4 (75:1),
(17) a content ratio of the Picloram to the uracil compound is 25:16 (1.5625:1) to 100:4 (25:1),
(18) a content ratio of the Fluroxypyr to the uracil compound is 50:16 (3.125:1) to 200:4 (50:1),
(19) a content ratio of the Triclopyr to the uracil compound is 125:16 (7.8125:1) to 500:4 (125:1),
(20) a content ratio of the MCPA to the uracil compound is 75:16 (4.6875:1) to 300:4 (75:1),
(21) a content ratio of the Mecoprop to the uracil compound is 200:16 (12.5:1) to 800:4 (200:1),
(22) a content ratio of the Quinclorac to the uracil compound is 50:16 (3.125:1) to 200:4 (50:1),
(23) a content ratio of the MCPB to the uracil compound is 75:16 (4.6875:1) to 300:4 (75:1),
(24) a content ratio of the Chloridazon to the uracil compound is 175:16 (10.9375:1) to 700:4 (175:1),
(25) a content ratio of the Bentazone to the uracil compound is 125:16 (7.8125:1) to 500:4 (125:1),
(26) a content ratio of the Bromoxynil to the uracil compound is 50:16 (3.125:1) to 200:4 (125:1),
(27) a content ratio of the Propanil to the uracil compound is 375:16 (23.4375:1) to 1500:4 (375:1),
(28) a content ratio of the Mesosulfuron to the uracil compound is 2:4 (0.5:1) to 8:1,
(29) a content ratio of the Metsulfuron to the uracil compound is 1:4 (0.25:1) to 4:1,
(30) a content ratio of the Diflufenican to the uracil compound is 37.5:4 (9.375:1) to 150:1,
(31) a content ratio of the Nicosulfuron to the uracil compound is 5:4 (1.25:1) to 20:1,
(32) a content ratio of the Iodosulfuron to the uracil compound is 1.25:4 (0.3125:1) to 5:1,
(33) a content ratio of the Florasulam to the uracil compound is 1:4 (1:4) to 4:1,
(34) a content ratio of the Mesotrione to the uracil compound is 15:4 (3.75:1) to 60:1,
(35) a content ratio of the Isoxaflutole to the uracil compound is 12.5:4 (3.125:1) to 50:1,
(36) a content ratio of the Flufenacet to the uracil compound is 87.5:4 (21.875:1) to 350:1,
(37) a content ratio of the Sulfentrazone to the uracil compound is 75:4 (18.75:1) to 300:1,
(38) a content ratio of the Carfentrazone to the uracil compound is 2.5:4 (0.625:1) to 10:1,
(39) a content ratio of the Bensulfuron to the uracil compound is 10:10 (1:1) to 40:2.5 (16:1), and
(40) a content ratio of the Pyrazosulfuron to the uracil compound is 2.5:10 (0.25:1) to 10:2.5 (4:1).

2. The herbicidal composition of claim 1, wherein the composition further comprises a solid or liquid diluent and surface-active agent.

3. The herbicidal composition of claim 2, wherein the diluent or the surface-active agent is contained in an amount of 0.1-99.9 wt% based on the total weight of the composition.

4. The herbicidal composition of claim 1, wherein the herbicidal composition is in the form of wettable powder, suspensions, emulsifible concentrates, emulsions, microemulsions, soluble concentrates, dispersible concentrates, water dispersible granules, granules, powder, suspension concentrates, water floating granules, or tablets.

5. The herbicidal composition of claim 1, wherein the active ingredients further include at least one selected from the group consisting of acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (ESPS), glutamine synthetase inhibitors, lipid biosynthesis inhibitors, mitosis inhibitors, protoporphyrinogen IX oxidase inhibitors, photosynthesis inhibitors, synergists, growth substances and cell wall biosynthesis inhibitors.

* * * * *